United States Patent [19]

Henzi

[11] 4,085,098

[45] Apr. 18, 1978

[54] AZO DYES CONTAINING A HETEROCYCLIC RING HAVING A QUATERNIZED NITROGEN ATOM AND AT LEAST ONE OPTIONALLY SUBSTITUTED PHENOXYALKYL OR NAPHTHYLOXYALKYL SUBSTITUENT

[75] Inventor: Beat Henzi, Neuallschwil, Switzerland

[73] Assignee: Sandoz Ltd., Basel, Switzerland

[21] Appl. No.: 383,877

[22] Filed: Jul. 30, 1973

[30] Foreign Application Priority Data

| | | |
|---|---|---|
| Jul. 31, 1972 | Switzerland | 11354/72 |
| Dec. 7, 1972 | Switzerland | 17824/72 |
| Feb. 5, 1973 | Switzerland | 1618/73 |

[51] Int. Cl.$^2$ ...................... C09B 29/08; C09B 29/36; D06P 3/24; D06P 3/52

[52] U.S. Cl. ................................ 260/157; 260/146 R; 260/146 D; 260/147; 260/154; 260/156; 260/158; 260/162; 260/163

[58] Field of Search ............... 260/152, 154, 157, 156, 260/158, 162, 163, 164, 165, 146 R, 146 P, 147

[56] References Cited

U.S. PATENT DOCUMENTS

| | | | |
|---|---|---|---|
| 2,913,303 | 11/1959 | Baumann et al. | 260/158 X |
| 3,078,137 | 2/1963 | Baumann et al. | 260/157 X |
| 3,102,878 | 9/1963 | Baumann et al. | 260/157 X |
| 3,132,132 | 5/1964 | Suzuki et al. | 260/158 |
| 3,133,052 | 5/1964 | Merian et al. | 260/158 |
| 3,148,935 | 9/1964 | Pfitzner et al. | 260/157 X |
| 3,245,981 | 4/1966 | Stright | 260/158 |
| 3,438,963 | 4/1969 | Robbins | 260/157 |
| 3,585,182 | 6/1971 | Straley et al. | 260/157 |
| 3,679,656 | 7/1972 | Iizuka et al. | 260/157 |
| 3,763,140 | 10/1973 | Entschel et al. | 260/158 |

*Primary Examiner*—Floyd D. Higel
*Attorney, Agent, or Firm*—Gerald D. Sharkin; Richard E. Vila; Melvyn M. Kassenoff

[57] ABSTRACT

Disclosed are basic azo dyes, free from sulphonic acid groups, and of formula,

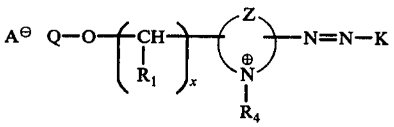

I in which

Q signifies an unsubstituted or substituted phenyl or naphthyl radical, $R_1$ signifies hydrogen, unsubstituted or substituted $C_{1-4}$ alkyl, phenyl or cyclohexyl, Z signifies a ring forming residue, $R_4$ signifies optionally substituted alkyl, alkenyl, alkoxy or cycloalkyl, K signifies a coupling component, A⊖ signifies an anion, and $x$ signifies 1, 2 or 3.

The dyes are useful for dyeing and printing textiles of polymers and copolymers of acrylonitrile and dicyanoethylene as well as synthetic polyamides and polyesters that have been modified to contain acid groups. The dyeings are level and exhibit good fastness to light, wet treatments, perspiration, sublimation, pressing and dry cleaning.

20 Claims, No Drawings

AZO DYES CONTAINING A HETEROCYCLIC RING HAVING A QUATERNIZED NITROGEN ATOM AND AT LEAST ONE OPTIONALLY SUBSTITUTED PHENOXYALKYL OR NAPHTHYLOXYALKYL SUBSTITUENT

The invention relates to basic azo compounds free from sulphonic acid groups.

The invention provides compounds of formula I,

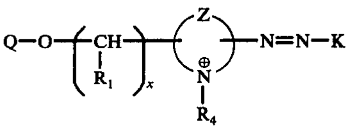

I in which

Q signifies a radical of formula

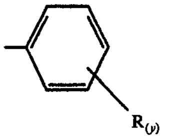

or

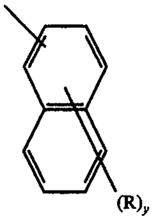

R signifies hydrogen; hydroxy; halogen; alkyl or alkoxy of 1 to 4 carbon atoms, unsubstituted or substituted by halogen, hydroxy, cyano, phenyl or phenoxy; trifluoromethyl; cycloalkyl of 5 or 6 carbon atoms, unsubstituted or substituted by alkyl of 1 to 4 carbon atoms; cyano; nitro; phenoxy; naphthyloxy; phenylazo;

or a radical of the formula —CORo, CO—ORo, —$SO_2$—Ro, —$SO_2$—NH—Ro, —$SO_2$—N(Ro)$_2$, O—CO—NH—Ro, —O—CO—N(Ro)$_2$, —CO—NH—Ro,

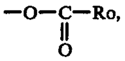

—CO—N(Ro)$_2$, —NH—CO—Ro, —$OSO_2$N-(Ro)$_2$, —$OSO_2$NHRo,

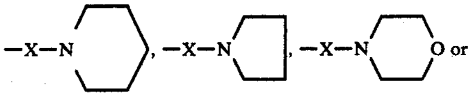

or

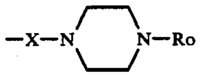

in which the Ro's, independently, signify $C_{1-4}$alkyl or phenyl, and X signifies —CO— or —$SO_2$—, $R_1$ signifies hydrogen; alkyl- of 1 to 4 carbon atoms, unsubstituted or substituted by halogen, $C_{1-4}$alkoxy or phenoxy; phenyl; or $C_{5-6}$ cycloalkyl;

Z signifies a residue which together with the nitrogen atom forms an unsaturated heterocyclic ring containing at least five ring atoms, which may be carbon, oxygen, sulphur or further nitrogen atoms, which ring optionally has an aromatic carbocyclic or heterocyclic ring fused thereto and is, along with any ring fused thereto, optionally substituted by substituents selected from alkyl of 1 to 4 carbon atoms and alkoxy of 1 to 4 carbon atoms, each unsubstituted or substituted by phenyl, phenoxy, hydroxy, —$CONH_2$, cycloalkyl of 5 or 6 carbon atoms, cyano or halogen; alkenyl of 2 to 4 carbon atoms; alkenyl of 2 to 4 carbon atoms substituted by hydroxy, halo, cyano, phenyl or carbamoyl; cycloalkyl of 5 to 7 carbon atoms, unsubstituted or substituted by $C_{1-4}$ alkyl, $C_{1-4}$ alkoxy or halogen; phenyl or phenoxy, each unsubstituted or substituted by cyano, nitro, $C_{1-4}$ alkyl, $C_{1-4}$ alkoxy or halogen; a radical of the formula —CO—Ro,

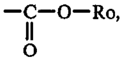

—NH—$SO_2$—Ro, —CO—NHRo, —CO—N-(Ro)$_2$, —NH—CO—Ro, —$SO_2$—Ro, —$SO_2$—N-(Ro)$_2$ or —$SO_2$—NHRo, in which Ro is as defined above; or phenylazo; the

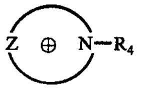

group being free from water-solubilizing groups and containing at least one quaternary nitrogen atom, and being bound to the azo group through a carbon atom, $R_4$ signifies a $C_{1-8}$ alkyl, $C_{2-8}$ alkenyl or $C_{1-4}$ alkoxy radical, each unsubstituted or substituted by halogen, hydroxy, phenyl, cycloalkyl of 5 or 6 carbon atoms, alkoxy of 1 to 4 carbon atoms or —$CONH_2$; or a cycloalkyl radical of 5 or 6 carbon atoms, unsubstituted or substituted by $C_{1-4}$ alkyl, $C_{1-4}$ alkoxy, halogen or hydroxy;

$y$ signifies 1, 2, 3, 4 or 5, and, when $y$ signifies 2 or more, the R's may be the same or different, $x$ signifies 1, 2 or 3, A⊖ signifies an organic or inorganic anion, and K signifies a coupling component free from water-solubilizing groups.

In the compounds of formula I, any heterocyclic ring

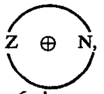

preferably contains 5 or 6 ring carbon atoms and preferably contains 1, 2 or 3 heteroatoms.

As examples of radicals

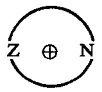

may be given thiazolyl, isothiazolyl, thiadiazolyl, triazolyl, imidazolyl, indazolyl, oxazolyl, pyridinyl, pyrimidinyl, pyridazinyl, pyrazinyl, benzothiazolyl, oxadiazolyl, quinoxalinyl, cinnolinyl, quinolinyl, phthalazinyl, pyrazolyl, benzoxazolyl and benzimidazolyl derivatives.

Preferred examples of

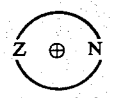

are the triazolyl, benzothiazolyl, quinolinyl and indazolyl derivatives, more preferably the triazolyl, pyridinyl and benzothiazolyl derivatives and most preferably the triazolyl derivatives.

As examples of anions A⊖ may be given the halides, such as chloride, bromide or iodide, sulphate, disulphate, methylsulphate, aminosulphate, perchlorate, carbonate, bicarbonate, phosphate, phosphormolybdate, phosphortungstenate, phosphortungstenmolybdate, formate, benzenesulphonate, naphthalenesulphonate, 4-chlorobenzenesulphonate, oxalate, maleinate, acetate, propionate, lactate, succinate, chloroacetate tartrate, malate, methanesulphonate or benzoate ions, or complex anions such as zinc chloride double salts, e.g. $ZnCl_3^{\ominus}$. The preferred anions are the chloride ions, methylsulphate ions, $ZnCl_3^{\ominus}$ ions and acetate ions.

The invention also provides a process for the production of compounds of formula I, characterised by quaternising a compound of formula II,

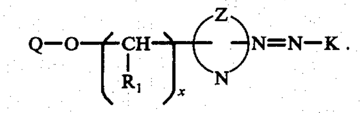

II in which Q, $R_1$, x, Z and K are as defined above, by reaction with a compound of formula III, $$R_4 — A \qquad III$$

in which $R_4$ is as defined above, and A corresponds to A⊖, above, or by addition reaction of an $R_4$ yielding epoxide or vinyl compound with a compound of formula II in the presence of water and with neutralization employing an acid HA.

The quaternisation with a compound of formula III may be carried out in conventional manner. Suitably, the reaction is carried out in an inert solvent, in an aqueous suspension or, where liquid under the reaction conditions, in an excess of the compound of formula III. Where necessary, the reaction can be carried out at elevated temperatures and in a buffered medium. As examples of preferred quaternising agents of formula III may be given methyl or ethyl chloride, bromide or iodide, alkyl sulphates, such as dimethyl sulphate, or benzyl chloride. As examples of other quaternising agents may be given acrylic acid amide hydrochloride, such as $CH_2=CH—CO—NH_2/HCl$, chloroacetic acid amide or epoxides such as ethylene oxide and propylene oxide, and epichlorohydrins, in the presence of an acid of the formula HA.

The compounds of formula II and III are either known or may be obtained in conventional manner from available starting materials.

Alternatively, the compounds of formula I may be obtained by coupling the diazo derivative of an amine of formula IV,

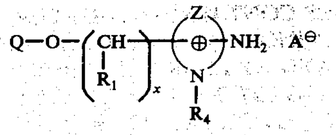

(IV)

in which Q, $R_1$, Z, $R_4$, x and A⊖ are as defined above, with a coupling component of formula V, $$H — K \qquad (V)$$

in which K is as defined above.

The coupling reaction can be carried out in conventional manner, for example as described in German Offenlegungsschrift No. 2,201,073. Thus, for example, the reaction can be carried out in aqueous medium at a temperature of from $-10°$ to $+20°$ C. The medium may be buffered acid, neutral or alkaline.

In the compounds of formula I, where Q signifies a naphthalene radical, such radical is preferably unsubstituted.

Preferred compounds of formula I are the compounds of formula I',

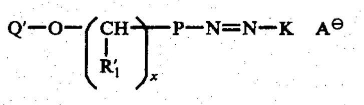

I' in which P signifies a radical of the formula

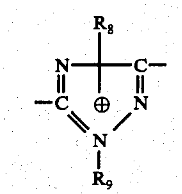

(a)

an isomer thereof of the formula

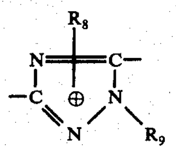

(b)

or

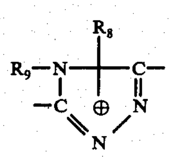

(c)

in which $R_8$ signifies an alkyl radical of 1 to 4 carbon atoms or alkenyl radical of 2 to 4 carbon atoms, unsubstituted or substituted by hydroxy, halogen, cyano, phenyl or $—CONH_2$; or a cyclohexyl radical, unsubstituted or substituted by $C_{1-4}$ alkyl, $R_9$ signifies an alkyl radical of 1 to 4 carbon atoms or alkenyl radical of 2 to 4 carbon atoms, unsubstituted or substituted by hydroxy, halogen, cyano, phenyl or $—CONH_2$; a cyclohexyl radical, unsubstituted or substituted by $C_{1-4}$ alkyl; or a phenyl radical, unsubstituted or substituted by halogen, $C_{1-4}$ alkyl or $C_{1-4}$ alkoxy;

a radical of the formula

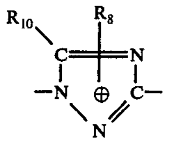
(d)

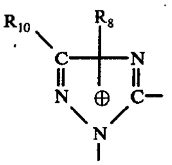
(e)

or

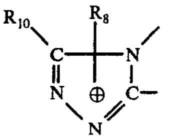
(f)

in which $R_8$ is as defined above, and $R_{10}$ signifies hydrogen or one of the significances of $R_9$, above, a radical of the formula

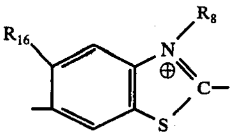
(g)

in which $R_8$ is as defined above, and $R_{16}$ signifies hydrogen; halogen; $C_{1-4}$ alkyl or $C_{1-4}$ alkoxy, unsubstituted or substituted by phenyl, phenoxy, hydroxy, —$CONH_2$, cycloalkyl of 5 or 6 carbon atoms, cyano or halogen; phenoxy; or a radical of the formula —CO—Ro, $$-\underset{\underset{O}{\|}}{C}-O-Ro,$$

—NH—$SO_2$—Ro, —CO—NH—Ro, —CON($Ro)_2$, —NH—CO—Ro, —$SO_2$—Ro, —$SO_2$—NH—Ro or —$SO_2$—N($Ro)_2$; in which Ro is as defined above;

or a radical of the formula

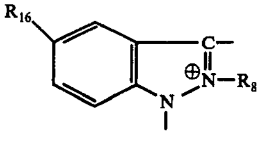
(h)

in which $R_8$ and $R_{16}$ are as defined above,

Q' signifies an unsubstituted naphthalene radical, an unsubstituted phenyl radical or a phenyl radical substituted by up to 5 halogen atoms or up to two substituents selected from nitro; halogen; hydroxy; cyano; trifluoromethyl; alkyl or alkoxy of 1 to 4 carbon atoms, unsubstituted or substituted by phenyl or phenoxy; cyclohexyl; phenoxy; benzoyloxy; phenylazo; dialkylsulfamoyloxy; a group of the formula —CORo, $$-\underset{\underset{O}{\|}}{C}-ORo,$$

—$SO_2$—Ro, —$SO_2$—NH—Ro, —$SO_2$—N($Ro)_2$, —CO—NH—Ro, —CO—N($Ro)_2$, —O—CO—NH—Ro; —O—CO—N—($Ro)_2$; or —NH—CO—Ro, in which Ro is as defined above;

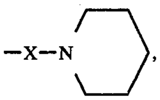, or 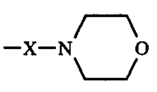

in which X is as defined above, $x$ signifies 1, 2 or 3, preferably 1 or 2, $A^\ominus$ is as defined above, preferably a halide, $ZnCl_3^\ominus$, methylsulfate or acetate ion, $R'_1$ signifies hydrogen, phenyl or $C_{1-4}$ alkyl, and K is as defined above.

As will be appreciated, formulae (b) and (c) above and (e) and (f) are isomers respectively of formulae (a) and (d). For convenience only one of the respective isomers will be given hereafter, being understood to embrace the isomers. Mixtures of the respective isomers are obtained when producing the compounds.

In the compounds of formula I', Q' preferably signifies an unsubstituted naphthalene radical or, alternatively, a phenyl radical substituted by up to 5 halogen, preferably chlorine, atoms or by up to two substituents, which may be the same or different, selected from halogen, preferably chlorine, nitro, hydroxy, cyano, alkyl of 1 to 4 carbon atoms, preferably methyl, alkoxy of 1 to 4 carbon atoms, preferably methoxy, trifluoromethyl, —CO—Ro, preferably methylcarbonyl or phenylcarbonyl, $$-\underset{\underset{O}{\|}}{C}-ORo,$$

preferably $C_{1-2}$ alkoxycarbonyl, —$SO_2$—Ro, preferably methylsulfonyl or phenylsulphonyl, —$SO_2$—NH—Ro or —$SO_2N(Ro)_2$, preferably dimethylaminosulphonyl, —NH—CO—Ro, preferably phenylcarbonylamino, —CO—NH—Ro or —CO—N($Ro)_2$, preferably monophenylaminocarbonyl, phenoxy, cyclohexyl, phenyl substituted $C_{1-4}$ alkyl, preferably benzyl, or phenoxy substituted $C_{1-4}$ alkyl, preferably phenoxymethyl. Where Q signifies a substituted phenyl radical, other than a halo substituted phenyl radical, such phenyl radical is generally monosubstituted, with the exception of where Q has a particularly preferred significance of 3-hydroxy-4-phenylcarbonylphenyl.

In the compounds of formula I', $R_1'$, preferably signifies a hydrogen atom or an alkyl radical pf 1 to 4 carbon atoms, more preferably a hydrogen atom or a methyl radical, and most preferably a hydrogen atom. P preferably signifies a radical of formula (a) or an isomer thereof or a radical of formula (d) or an isomer thereof. $R_8$ preferably signifies an alkyl radical of 1 to 4 carbon atoms, unsubstituted or substituted by hydroxy, or —

$CONH_2$, e.g. methyl, ethyl, propyl, 2-hydroxyethyl, 2-hydroxypropyl and 2-carbamoyl ethyl, more preferably an unsubstituted alkyl radical, and most preferably a methyl radical. $R_9$ preferably signifies an unsubstituted cyclohexyl radical or an alkyl radical of 1 to 4 carbon atoms, unsubstituted or substituted by hydroxy, —$CONH_2$ or phenyl, e.g. methyl, ethyl, propyl, 2-hydroxyethyl, 2-hydroxypropyl, 2-carbamoyl ethyl and benzyl, more preferably an unsubstituted alkyl radical and most preferably a methyl radical. $R_{10}$ preferably signifies hydrogen. $R_{16}$ preferably signifies hydrogen, $C_{1-4}$ alkyl or alkoxy or di-$C_{1-4}$ alkylaminosulphonyl, preferably hydrogen, methoxy or dimethylaminosulphonyl.

In the compounds of formulae I and I', K may be, for example, of the benzene, naphthalene, heterocyclic or aliphatic series of coupling components. Suitable significances of K will suggest themselves to those skilled in the art and, as will be appreciated, the particular significance of K is of minor consequence in the invention. As examples of significances of K may be given

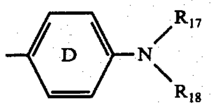
(p)

in which
- ring D is further unsubstituted or further substituted, other than by water-solubilizing groups, cationic groups and aryloxyalkyl groups, and
- either $R_{17}$ and $R_{18}$, which may be the same or different, each signifies hydrogen or an optionally substituted hydrocarbon radical, or
- $R_{17}$ and $R_{18}$, together with the nitrogen atom, for a saturated or partially saturated heterocyclic radical,

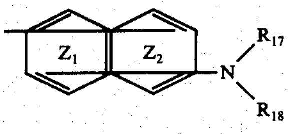
(q)

in which rings
- $Z_1$ and $Z_2$ are further unsubstituted or substituted, other than by water-solubilizing groups, cationic groups and aryloxyalkyl groups,
- $R_{17}$ and $R_{18}$ are as defined above, and

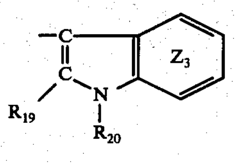
(r).

in which
- $R_{19}$ signifies an optionally substituted hydrocarbon radical,
- $R_{20}$ signifies hydrogen or an optionally substituted hydrocarbon radical, and
- ring $Z_3$ is unsubstituted or substituted, other than by water-solubilizing groups, cationic groups and aryloxyalkyl groups.

Where K has significance (p), above, preferred significances are of the formula

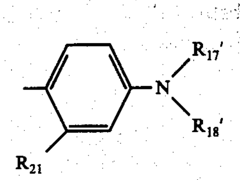
(p')

in which
- either $R_{17}'$ and $R_{18}'$, which may be the same or different, each siginifies hydrogen; cyclohexyl; phenyl; $C_{1-4}$ alkyl, unsubstituted or substituted by $C_{1-4}$ alkoxycarbonyl, phenylcarbonyloxy, phenoxy, halogen, hydroxy, phenyl, cyano, $C_{1-4}$ alkoxy, $C_{1-4}$ alkylcarbonyloxy or N,N-di ($C_{1-4}$) alkylaminocarbonyloxy, e.g. N,N-dimethylaminocarbonyloxyethyl, or
- $R_{17}'$ and $R_{18}'$, together with the nitrogen atom, are linked to form

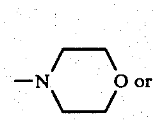 or 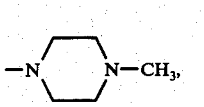,

- $R_{21}$ signifies a hydrogen atom, a $C_{1-4}$ alkyl or alkoxy radical or a halogen atom.

Preferred significances of $R_{17}'$ and $R_{18}'$ are unsubstituted $C_{1-4}$ alkyl, more preferably methyl or ethyl, and most preferably ethyl; ethoxycarbonylethyl, phenylcarbonyloxyethyl, chloroethyl, hydroxyethyl, benzyl, cyanoethyl, methoxyethyl, phenyl, methylcarbonyloxyethyl, phenoxyethyl or, together, —$C_2H_4$—O—$C_2H_4$— and —$C_2H_4$—$N(CH_3)$—$C_2H_4$—. The most preferred significance of $R_{17}'$ and $R_{18}'$ is ethyl.

Preferred significances of $R_{21}$ are hydrogen, methyl and methoxy, hydrogen being most preferred.

Where K signifies (q), above, preferred significances are of the formula

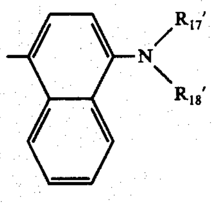
(q')

in which the significances of $R_{17}'$ and $R_{18}'$ and the preferred significances are as set out above.

Where K signifies (r), above, preferred significances are of the formula

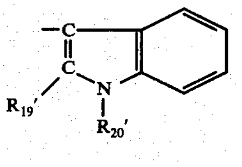
(r')

in which
- $R_{19}'$ signifies phenyl or $C_{1-4}$ alkyl, preferably methyl, unsubstituted or substituted by phenyl, e.g. benzyl, and
- $R_{20}'$ signifies hydrogen, $C_{1-4}$ alkyl, preferably methyl, or phenyl.

Other representative significances of K are, for example

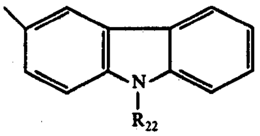

(s)

in which $R_{22}$ signifies $C_{1-4}$ alkyl, preferably ethyl,

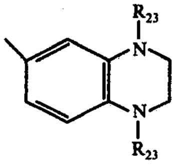

(t)

in which the $R_{23}$'s, which may be the same or different, each signifies $C_{1-4}$ alkyl, preferably methyl,

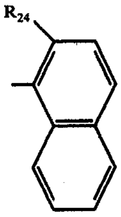

(u)

in which $R_{24}$ signifies $—NH_2$, —OH or $—NH—R_{26}$, in which $R_{26}$ signifies phenyl, unsubstituted or substituted by up to two methyl radicals,

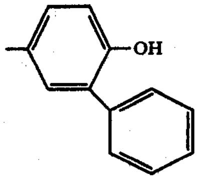

(v)

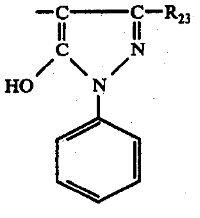

(w)

in which $R_{23}$ is as defined above,

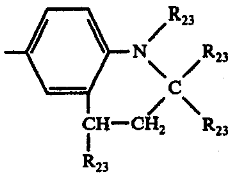

(x)

in which the $R_{23}$'s, which are the same or different and are as defined above, and

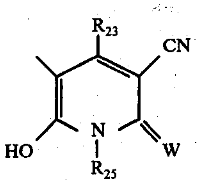

(y)

in which $R_{23}$ is as defined above, $R_{25}$ signifies hydrogen or an alkyl radical of 1 to 4 carbon atoms, e.g. methyl or ethyl, unsubstituted or substituted by $C_{1-4}$ alkoxy, preferably methoxy, and W signifies O or NH, preferably O.

Representative of the compounds of formula I' are the compounds of formula

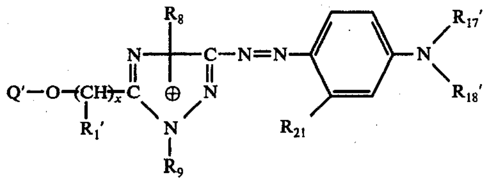

Ia' in which Q', $R_1'$, $x$, $R_8$, $R_9$, $R_{21}$, $R_{17}'$ and $R_{18}'$ are as defined above.

Preferred compounds of formula Ia' are the compounds of formula Ia'',

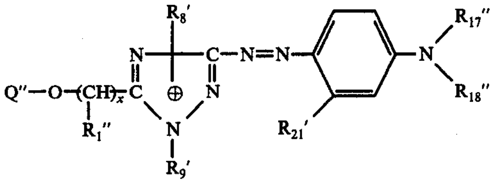

in which $R_8'$ signifies $C_{1-4}$, preferably $C_{1-2}$, alkyl, unsubstituted or substituted by a hydroxy radical or the group $—CONH_2$, $R_9'$ signifies a $C_{1-4}$, preferably $C_{1-2}$, alkyl radical unsubstituted or substituted by hydroxy or $—CONH_2$; or cyclohexyl, $R_{17}''$ and $R_{18}''$, which may be the same or different, each signifies phenyl, $C_{1-4}$ alkyl, unsubstituted or substituted by $C_{1-4}$ alkokycarbonyl, e.g. ethoxycarbonyl, phenylcarbonyloxy, phenoxy, halogen, preferably chlorine, hydroxy, phenyl, e.g. benzyl, cyano, $C_{1-4}$ alkoxy, e.g. methoxy, alkylcarbonyloxy, e.g. methylcarbonyloxy, or, together, $—C_2H_4—O—C_2H_4—$ or

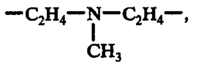

$R_{21}'$ signifies hydrogen, $C_{1-4}$ alkyl, preferably methyl, $C_{1-4}$ alkoxy, preferably methoxy, or halogen, preferably chlorine, $R_1''$ signifies hydrogen or methyl, x' signifies 1, 2 or 3, and Q'' signifies an unsubstituted naphthyl radical, preferably a 2-naphthyl radical, an unsubstituted phenyl radical, a phenyl radical substituted by up to 5 halogen, preferably chlorine, atoms or by up to two substituents selected from hydroxy, phenylcarbonyl, halogen, preferably chlorine, $C_{1-4}$ alkyl, preferably methyl, $C_{1-4}$ alkoxy, preferably methoxy, nitro, $CF_3$, $C_{1-4}$ alkylcarbonyl, preferably methylcarbonyl, cyano, $C_{1-4}$ alkoxycarbonyl, preferably ethoxycarbonyl, phenylcarbonyloxy, alkylsulphonyl, preferably methylsulphonyl, dialkylaminosulphonyl, preferably dimethylaminosulphonyl, dialkylaminosulphonyloxy, preferably dimethylaminosulphonyloxy, phenylcarbonylamino, phenylsulphonyl, benzyl, cyclohexyl, phenoxy, phenylaminocarbonyloxy, $C_{1-4}$ alkylaminocarbonyloxy, N-phenyl-N-$C_{1-4}$ alkylaminocarbonyloxy, phenoxymethyl phenylazo.

In the compounds of formula Ia'', Q'' preferably signifies an unsubstituted phenyl or naphthyl radical or a phenyl radical substituted by up to five chlorine atoms, by a 3-hydroxy group and a 4-phenylcarbonyl group, or by one of the aforementioned possible substituents in the 4-position. Most preferably, Q'' signifies an unsubstituted phenyl or naphthyl radical or a phenyl radical substituted by up to 5 chlorine atoms. $R_8'$ and $R_9'$ both preferably signify methyl radicals. x' preferably signifies 1 or 2. $R_{21}'$ preferably signifies hydrogen. $R_{17}''$ preferably signifies a methyl or ethyl radical, and $R_{18}'$ preferably signifies a methyl, ethyl, benzyl or butoxycarbonylethyl radical.

Other representative compounds of formula I' are the compounds of formula Iaa',

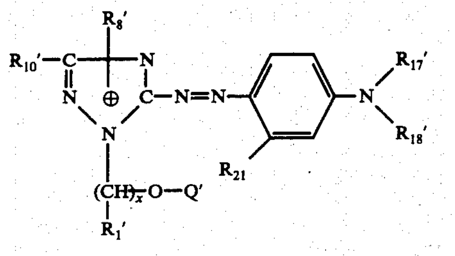

(Iaa')

in which $R_1'$, $R_8'$, $R_{17}'$, $R_{18}'$, $R_{21}'$, Q' and x are as defined above, and $R_{10}'$ signifies hydrogen or one of the significances of $R_9'$, above.

Preferred compounds of formula Iaa' are the compounds of formula Iaa'',

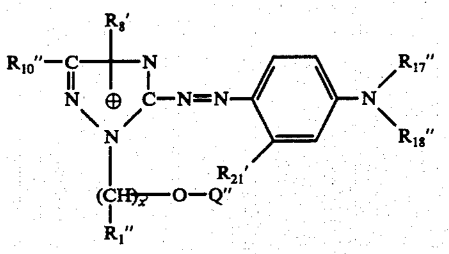

Iaa'' in which $R_1''$, $R_8'$, $R_{17}''$, $R_{18}''$, $R_{21}'$, x' and Q'' are as defined above, and $R_{10}''$ signifies hydrogen or one of the significances of $R_9'$, above.

$R_{10}''$ preferably signifies hydrogen, and the preferred significances of $R_1''$, $R_8'$, $R_{17}''$, $R_{18}''$, $R_{21}'$, x' and Q'' are as defined above.

As examples of alkyl and alkoxy radicals of 1 to 4 carbon atoms, as used herein, may be given methyl, ethyl, n-propyl, isopropyl and n-butyl and the corresponding alkoxy radicals. Unless otherwise stated, the preferred such radicals are methyl, ethyl, methoxy and ethoxy, methyl and methoxy being most preferred. By the term halogen, as used herein, is meant chlorine, bromine and iodine, chlorine and bromine being preferred, chlorine being most preferred.

The compounds of formula I are useful as dyes. They may be converted into dyeing preparations, e.g. into stable, liquid or solid dyeing preparations, in conventional manner, e.g. by grinding or granulating or dissolving in conventional dyestuff solvents, if necessary with the addition of assistants such as stabilizers. Such preparations may be produced for example, in accordance with French Pat. Nos. 1,572,030 and 1,581,900.

The compounds of formula I may be used in the dyeing or printing of textile substrates, whether in fibre, yarn or fabric form, which consist of or comprise homopolymers or co-polymers of acrylonitrile or asymmetrical dicyanoethylene. The dyeing of such substrates may be carried out in conventional manner.

The compounds of formula I may also be used for dyeing or printing substrates of synthetic polyamide or synthetic polyester fibers, modified by the introduction of acid groups. Polyamides of this type are described in Belgian Pat. 706,104 and polyester fibres of this type are described in U.S. Pat. No. 3,379,723. The dyeing of such substrates may be carried out in conventional manner. It is advantageous to dye in an aqueous, neutral or acid medium, at from 60° C to the boil or at temperatures above 100° C under pressure.

The dyeings obtained with the compounds of formula I are level, have stable light fastness as well as good wet fastness properties, e.g. to washing, perspiration, sublimation, pleating, decatizing, pressing, steam, water, sea water, dry cleaning, cross-dyeing and solvents. The dyes are well soluble in water, show good compatibility with salt, good stability to boiling, good pH stability and partly reserve fibres other than those on which they are dyeable. Further, they possess good power of build-up in combination with other basic dyes.

The compounds, which have good solubility in organic solvents, may also be used for the dyeing of natural or synthetic resins in the mass, being incorporated therein in conventional manner, e.g. by intimate admixture therein, for example by milling, optionally with the use of a solvent.

It has been found that mixtures of two or more of the compounds of the present invention or of one of the compounds of the present invention and other cationic dyes can be used with advantage.

The following Examples, in which parts and percentages are by weight and temperatures are in degrees centigrade, illustrate the invention.

EXAMPLE 1

19 Parts of 3-phenoxymethyl-5-amino-1,2,4-triazole are dissolved in 150 parts of glacial acetic acid at 70° and diluted with 10 parts of propionic acid and 18 parts of phosphoric acid. The mixture is cooled to a temperature between −5° and 0° and 21 parts of a solution of 4N. sodium nitrite are added thereto. Over a period of 30 minutes, the diazo solution is added dropwise into a solution consisting of 15 parts N,N-diethylaniline, 5 parts aminosulphonic acid and 50 parts glacial acetic acid. Simultaneously, 100 parts of ice are added and the temperature is maintained at 0°-5°. The dye solution is diluted with 160 parts of isopropanol and 100 parts of ice and the pH is adjusted to 5 by the addition of 110 parts of sodium acetate. With further stirring a crystalline dye is obtained. It is filtered, washed twice, each time with 100 parts of water and dried at 50° under vacuum.

30.5 Parts of the dried and finely ground dye are stirred into 300 parts of butanol, 3.5 parts magnesium oxide and 25 parts of dimethylsulphate are added and the suspension is heated to a temperature between 45° and 50° for 3 hours. After cooling to room temperature the dye solution is shaken twice, each time with 150 parts of a 26% brine, and evaporated under vacuum at a temperature of between 50° and 60°. The residue is dissolved in 300 parts of water at 80°, 15 parts of "Hyflo" and 10 parts of "Norit Supra" are added and after 15 minutes is filtered using a talc filter. The filtrate is washed with 750 parts of water at 50° and the dye is salted out with 15 parts of zinc chloride and 55 parts of sodium chloride. Stirring is effected overnight and the crystalline dye is filtered with suction and washed with 100 parts of 5% sodium chloride solution. After drying at 40° under vacuum, 30.8 parts of the dye of the formula

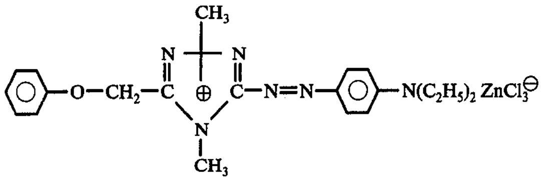

are obtained, which give bluish-red dyeings on polyacrylonitrile fibres and acid-modified polyester fibres.

EXAMPLE 2

Instead of the 3-phenoxymethyl-5-amino-1,2,4-triazole in Example 1, 3-α-naphthoxymethyl-5-amino-1,2,4-triazole is used, employing the same process as Example 1, a similar dye of the formula

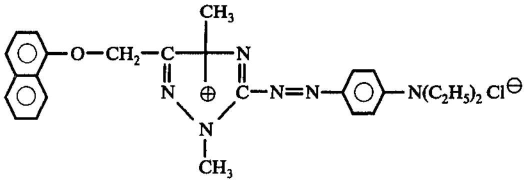

is obtained, which gives the same bluish-red dyeings on polyacrylonitrile fibres and acid modified polyester fibres.

3-Phenoxymethyl-5-amino-1,2,4-triazole can be obtained in the following manner:

69.5 Parts of aminoguanidine bicarbonate and 91.4 parts of phenoxyacetic acid are melted together at a temperature between 180° to 190° for 2 hours. After cooling to 130° the reaction mixture is mixed with 400 parts of cellosolve and 400 parts of conc. hydrochloric acid. The mixture is heated under reflux for 12 hours and left to cool. The resulting product is filtered with suction and washed with a little cellosolve. 108 Parts of the desired product are obtained. By crystallizing from a solvent of acetone and carbon tetrachloride 3-phenoxymethyl-5-amino-1,2,4-triazole with a melting point of 185°-186° is obtained.

The structural composition of further dyes is shown in the following Table I; they can be produced in accordance with the procedure of Examples 1 and 2 and agree with the formula

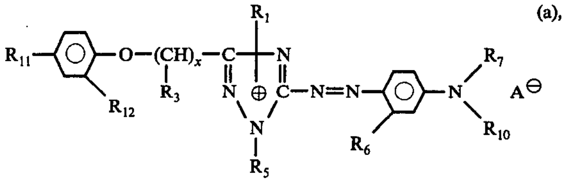

(a), wherein $R_1$, $R_3$, $R_5$—$R_7$, $R_{10}$—$R_{12}$ and X have the significances as given in the Table I.

The anion A⊖ may be any of those given in the foregoing description.

Table I
| Example No. | $R_1$ | $R_5$ | $R_6$ | $R_3$ | $R_{11}$ | $R_{12}$ | $R_7$ | $R_{10}$ | x | (I) |
|---|---|---|---|---|---|---|---|---|---|---|
| 3 | $-CH_3$ | $-CH_3$ | H | H | Cl— | H | $-C_2H_5$ | $-C_2H_5$ | 1 | bluish-red |
| 4 | " | " | H | H | $-CH_3$ | H | " | " | 1 | " |
| 5 | " | " | H | H | $-OCH_3$ | H | " | " | 1 | " |
| 6 | " | " | H | H | $-NO_2$ | H | " | " | 1 | " |
| 7 | " | " | H | H | $-CF_3$ | H | " | " | 1 | " |
| 8 | " | " | H | H | $-COCH_3$ | H | " | " | 1 | " |
| 9 | " | " | H | H | $-CN$ | H | " | " | 1 | " |
| 10 | " | " | H | H | $-\underset{\underset{O}{\|}}{C}-OC_2H_5$ | H | " | " | 1 | " |
| 11 | " | " | H | H | 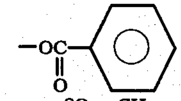 | H | " | " | 1 | " |
| 12 | " | " | H | H | $-SO_2-CH_3$ | H | " | " | 1 | " |
| 13 | " | " | H | H | $-SO_2-N(CH_3)_2$ | H | " | " | 1 | " |
| 14 | " | " | H | H | $-OSO_2N(CH_3)_2$ | H | " | " | 1 | " |
| 15 | " | " | H | H | 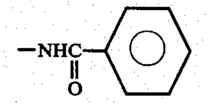 | H | " | " | 1 | " |
| 16 | " | " | H | H | 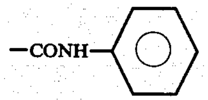 | H | " | " | 1 | " |
| 17 | " | " | H | H | 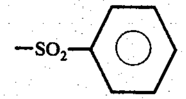 | H | " | " | 1 | " |
| 18 | " | " | H | H | 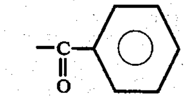 | H | " | " | 1 | " |
| 19 | " | " | H | H | 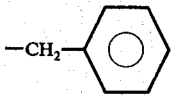 | H | " | " | 1 | " |
| 20 | " | " | H | H | 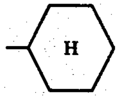 | H | " | " | 1 | " |
| 21 | " | " | H | H | 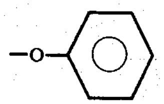 | H | " | " | 1 | " |

Table I-continued

| | | | | | | | | | | |
|---|---|---|---|---|---|---|---|---|---|---|
| 22 | " | " | H | H | 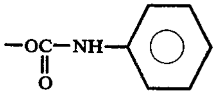 | H | " | " | 1 | " |
| 23 | " | " | H | H | 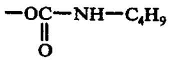 | H | " | " | 1 | " |
| 24 | " | " | H | H | 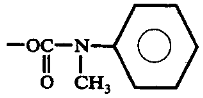 | H | " | " | 1 | " |
| 25 | " | " | H | H | 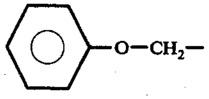 | H | " | " | 1 | " |
| 26 | " | " | H | H | 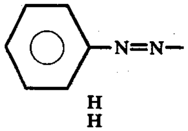 | H | " | " | 1 | scarlet |
| 27 | " | " | H | H | H | H | " | $-C_2H_4COOC_2H_5$ | 1 | red |
| 28 | " | " | H | H | H | H | " | 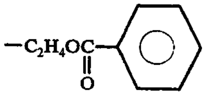 | 1 | bluish-red |
| 29 | " | " | H | H | H | H | " | 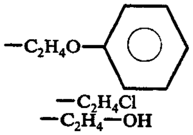 | 1 | " |
| 30 | " | " | H | H | H | H | $-C_4H_9$ | $-C_2H_4Cl$ | 1 | " |
| 31 | " | " | H | H | H | H | " | $-C_2H_4-OH$ | 1 | " |
| 32 | " | " | H | H | H | H | $-CH_3$ | 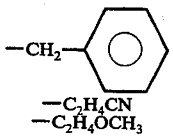 | 1 | " |
| 33 | " | " | H | H | H | H | " | $-C_2H_4CN$ | 1 | red |
| 34 | " | " | H | H | H | H | " | $-C_2H_4OCH_3$ | 1 | bluish-red |
| 35 | " | " | H | H | H | H | " | 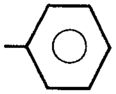 | | rubine |
| 36 | " | " | H | H | H | H | $-C_2H_5$ | 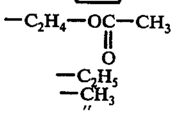 | 1 | bluish-red |
| 37 | " | " | $-CH_3$ | H | Cl | $-Cl$ | " | $-C_2H_5$ | 1 | " |
| 38 | " | " | $-OCH_3$ | H | H | H | $-CH_3$ | $-CH_3$ | 1 | " |
| 39 | " | " | $-Cl$ | H | H | H | " | " | 1 | scarlet |
| 40 | $-C_2H_5$ | $-C_2H_5$ | H | H | H | H | $-C_2H_5$ | $-C_2H_5$ | 1 | bluish-red |
| 41 | $-CH_2-CH_2OH$ | $-C_2H_4OH$ | H | H | H | H | " | " | 1 | strong bluish-red |

Table I-continued

| | | | | | | | | | | |
|---|---|---|---|---|---|---|---|---|---|---|
| 42 | $-CH_2-CH(CH_3)-OH$ | $-CH_2-CH(CH_3)-OH$ | H | H | H | H | " | " | 1 | " |
| 43 | $-C_2H_4CONH_2$ | $-C_2H_4CONH_2$ | H | H | H | H | " | " | 1 | bluish-red |
| 44 | $-CH_3$ | 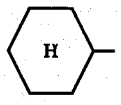 | H | H | H | H | " | " | 1 | " |
| 45 | " | 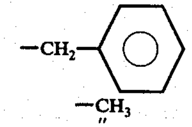 | H | H | H | H | " | " | 1 | " |
| 46 | " | $-CH_3$ | H | $-CH_3$ | H | H | $-CH_3$ | $-CH_3$ | 1 | " |
| 47 | " | " | H | " | H | H | $-C_2H_5$ | $-C_2H_5$ | 1 | " |
| 48 | " | " | H | " | H | H | " | 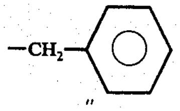 | 1 | " |
| 49 | " | " | H | " | H | H | $-CH_3$ | " | 1 | " |
| 50 | " | " | H | H | $-Cl$ | $-Cl$ | $-C_2H_5$ | $-C_2H_5$ | 1 | " |
| 51 | " | " | H | $-CH_3$ | H | H | $-CH_3$ | 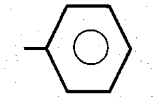 | 1 | rubine |
| 52 | " | " | H | " | H | H | $-C_2H_5$ | 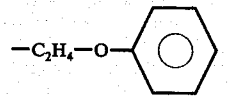 | 1 | bluish-red |
| 53 | " | " | H | " | H | H | " | $-C_2H_4Cl$ | 1 | " |
| 54 | " | " | $-CH_3$ | $-CH_3$ | H | H | " | $-C_2H_5$ | 1 | strong bluish-red |
| 55 | " | " | H | H | H | H | " | " | 2 | bluish-red |
| 56 | " | " | H | H | H | H | $-CH_3$ | $-CH_3$ | 2 | strong bluish-red |
| 57 | " | " | H | H | H | H | " | 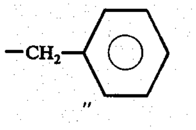 | 2 | " |
| 58 | " | " | H | H | H | H | $-C_2H_5$ | " | 2 | " |
| 59 | " | " | H | H | H | H | $-CH_3$ | 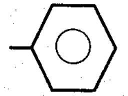 | 2 | rubine |
| 60 | " | " | H | H | $-Cl$ | $-Cl$ | $-C_2H_5$ | $-C_2H_5$ | 2 | bluish-red |
| 61 | " | " | $-CH_3$ | H | H | H | " | " | 2 | " |
| 62 | " | " | H | H | H | H | " | " | 3 | " |
| 63 | " | " | H | H | H | H | $-CH_3$ | 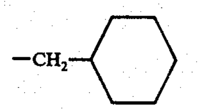 | 3 | " |

Table I-continued
| | | | | | | | $R_7$ together with $R_{10}$ | | |
|---|---|---|---|---|---|---|---|---|---|
| 64 | " | " | H | H | H | H | $-C_2H_4-O-C_2H_4-$ | 1 | " |
| 65 | " | " | H | H | H | H | " | 2 | " |
| 66 | " | " | H | H | H | H | $-C_2H_4-N(CH_3)-C_2H_4-$ | 1 | " |
| Ex. | | Dye shade on polyacrylonitrile |
|---|---|---|
| 67. | 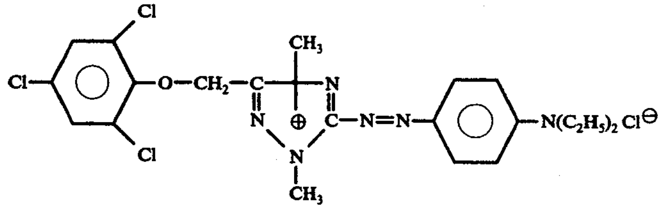 | bluish-red |
| 68. | 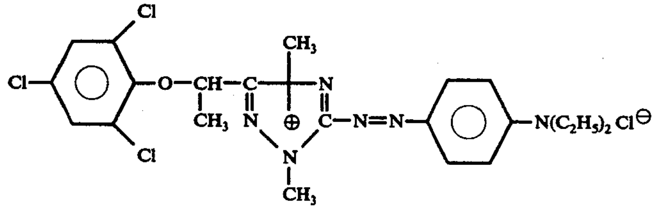 | " |
| 69. | 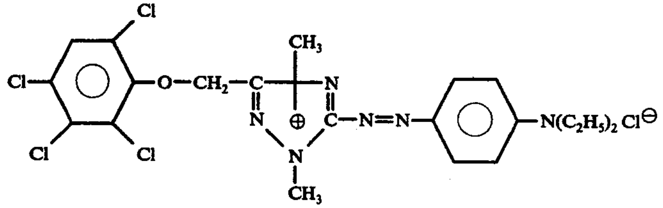 | " |
| 70. | 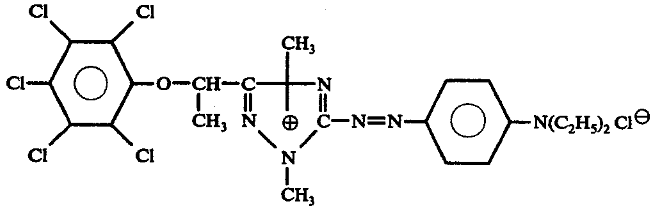 | " |

The structural composition of further dyes is shown in the following Table II; they can be produced in accordance with the procedure of Examples 1 and 2 and agree with the formula

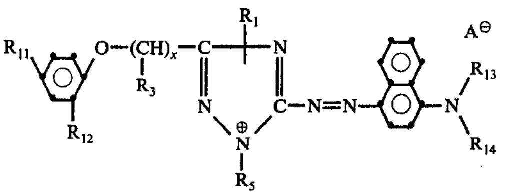
(b), wherein $R_1$, $R_3$, $R_5$, $R_{11}$ to $R_{14}$ and X have the significances as given in the columns. A further Column I indicates the dye shade on polyacrylonitrile and acid modified synthetic polyester and polyamide fibres. The anion A⊖ may be any of those given in the foregoing description.

The structural composition of further dyes is shown in the following Table III; the dyes can be produced in accordance with the procedure of Examples 1 and 2 and agree with the formula

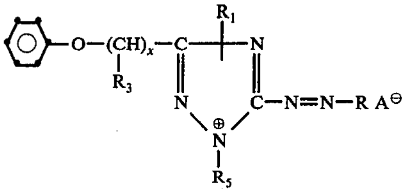
(c), in which R, $R_1$, $R_3$, $R_5$ and X have the significances as given in the columns of Table III. A further column indicates the dye shade on polyacrylonitrile fibres, acid modified polyester fibres and on polyamide fibres. The anion A⊖ may be any of those named in the foregoing description.

Table II

| Example | $R_1$ | $R_5$ | $R_{11}$ | $R_{12}$ | X | $R_3$ | $R_{13}$ | $R_{14}$ | I |
|---|---|---|---|---|---|---|---|---|---|
| 75 | $-CH_3$ | $-CH_3$ | H | H | 1 | H | $-CH_3$ | $-CH_3$ | bluish-violet |
| 76 | " | " | H | H | 1 | H | " | $-C_2H_5$ | " |
| 77 | " | " | H | H | 1 | H | " | $-C_2H_4COOC_2H_5$ | " |
| 78 | " | " | H | H | 1 | H | " | $-C_2H_4COOC_4H_9$ | " |
| 79 | " | " | H | H | 1 | $-CH_3$ | " | " | " |
| 80 | $-C_2H_5$ | $-C_2H_5$ | H | H | 1 | H | $-C_2H_5$ | $-C_2H_5$ | " |
| 81 | " | " | H | H | 1 | H | " | $-C_2H_4COOC_4H_9$ | ' |
| 82 | $-CH_3$ | " | $-Cl$ | H | 1 | $-CH_3$ | $-CH_3$ | " | " |
| 83 | " | " | " | Cl | 1 | " | " | " | " |
| 84 | " | $-CH_3$ | H | H | 2 | H | " | $-CH_3$ | reddish-violet |
| 85 | " | " | H | H | 2 | H | " | $-C_2H_5$ | " |
| 86 | $-CH_3$ | $-CH_3$ | H | H | 2 | H | $-CH_3$ | $-C_2H_4COOC_4H_9$ | reddish-violet |
| 87 | " | " | $-Cl$ | $-Cl$ | 1 | H | " | " | bluish-violet |
| 88 | " | " | " | " | 2 | H | " | " | " |

Table III

| Ex. | $R_1$ | $R_5$ | X | R | $R_3$ | I |
|---|---|---|---|---|---|---|
| 89 | $-CH_3$ | $-CH_3$ | 1 | 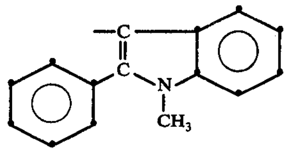 | H | reddish-yellow |
| 90 | " | " | 2 | " | H | " |
| 91 | $-C_2H_5$ | $-C_2H_5$ | 1 | " | H | " |
| 92 | " | " | 2 | " | H | " |
| 93 | $-CH_3$ | $-CH_3$ | 1 | 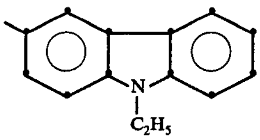 | $-CH_3$ | brownish-red |
| 94 | " | " | 2 | " | H | " |
| 95 | " | " | 1 | 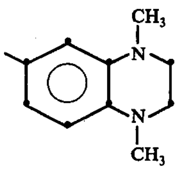 | H | bluish-red |
| 96 | " | " | 2 | " | H | " |

Table III-continued
| Ex. | $R_1$ | $R_5$ | X | R | $R_3$ | I |
|---|---|---|---|---|---|---|
| 97 | " | " | 1 | 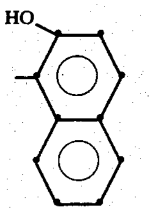 | H | scarlet |
| 98 | " | " | 2 | " | H | " |
| 99 | " | " | 1 | 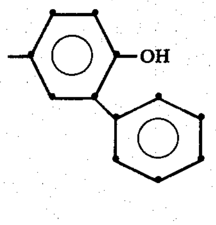 | H | orange |
| 100 | " | " | 2 | " | H | " |
| 101 | " | " | 1 | 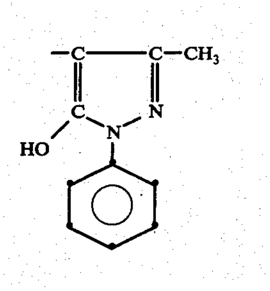 | H | greenish-yellow |
| 102 | " | " | 2 | " | H | " |
| 103 | $-CH_3$ | $-CH_3$ | 1 | 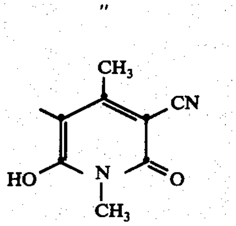 | H | reddish-yellow |
| 104 | " | " | 2 | " | H | " |
| 105 | " | " | 1 | 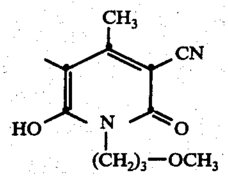 | $CH_3$ | " |
| 106 | " | " | 2 | " | H | " |
| 107 | " | " | 1 | 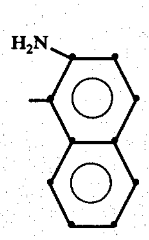 | $-CH_3$ | scarlet |
| 108 | " | " | 2 | " | H | " |

Table III-continued
| Ex. | $R_1$ | $R_5$ | X | R | $R_3$ | I |
|---|---|---|---|---|---|---|
| 109 | " | " | 1 | 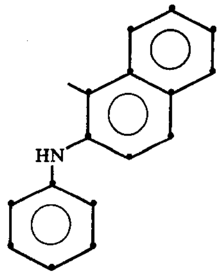 | H | bluish-red |
| 110 | " | " | 2 | " | H | " |
| 111 | " | " | 1 | 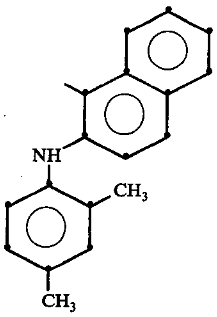 | H | bluish-red |
| 112 | " | " | 2 | " | H | " |
| 112a | $-CH_3$ | $-CH_3$ | 1 | 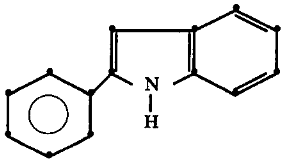 | H | bluish-red |
| 112b | " | " | 1 | 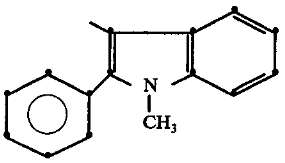 | H | " |
| 112c | " | " | 1 | 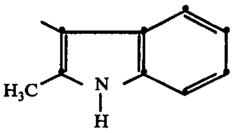 | H | " |
| 112d | " | " | 1 | 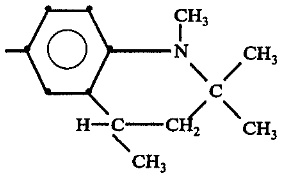 | H | " |
The structural composition of further dyes is shown in the following Table IV; the dyes may be obtained in accordance with the procedure of Examples 1 and 2 and agree with the formula
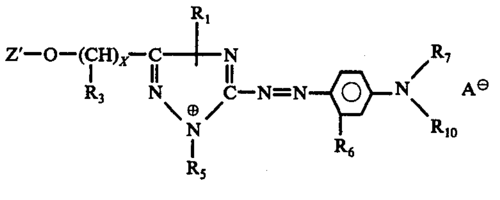
(d), in which Z′, $R_1$, $R_3$, $R_5$, $R_6$, $R_7$, $R_{10}$ and X have the significances given in the columns of Table IV. A further column I indicates the dye shade on polyacrylonitrile fibres, acid modified synthetic polyester fibres and polyamide fibres. The anion A⊖ may be any one of those named in the foregoing description.

Table IV

| Ex. | $R_1$ | $R_5$ | $R_3$ | $R_6$ | X | Z′ | $R_7$ | $R_{10}$ | I |
|---|---|---|---|---|---|---|---|---|---|
| 113 | $-CH_3$ | $-CH_3$ | H | H | 1 | 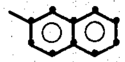 | $-CH_3$ | $-CH_3$ | strong bluish red |
| 114 | " | " | H | H | 1 | 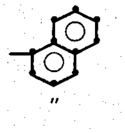 | " | " | " |
| 115 | " | " | H | H | 1 | " | " | $-CH_2-$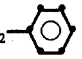 | " |
| 116 | " | " | H | H | 1 | 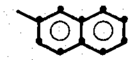 | " | " | " |
| 117 | " | " | H | H | 1 | " | $-C_2H_5$ | " | " |
| 118 | " | " | H | H | 1 | 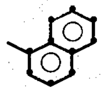 | " | " | " |
| 119 | " | " | H | H | 1 | " | " | $-C_2H_5$ | " |
| 120 | " | " | H | H | 1 | " | $-CH_3$ | 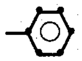 | rubine |
| 121 | " | " | $CH_3$ | H | 1 | 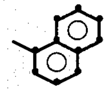 | " | " | " |
| 122 | " | " | H | $-CH_3$ | 1 | " | $-C_2H_5$ | $-C_2H_5$ | strong bluish-red |
| 123 | " | " | H | " | 1 | 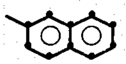 | " | " | |
| 124 | " | " | $-CH_3$ | H | 1 | " | " | " | " |
| 125 | " | " | " | H | 1 | 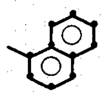 | " | " | " |
| 126 | " | " | " | H | 1 | " | " | $-CH_2-$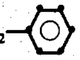 | " |
| 127 | " | " | " | H | 1 | 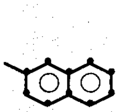 | " | " | " |
| 128 | " | " | " | H | 1 | " | $-CH_3$ | " | " |
| 129 | " | " | " | H | 1 | 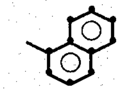 | " | " | " |
| 130 | " | " | H | H | 2 | 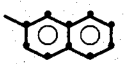 | $-CH_3$ | $-CH_3$ | bluish-red |
| 131 | " | " | H | H | 2 | 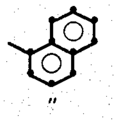 | " | " | " |
| 132 | " | " | H | H | 2 | " | " | $-CH_2-$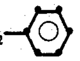 | " |
| 133 | " | " | H | H | 2 | 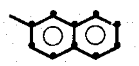 | " | " | " |
| 134 | " | " | H | H | 2 | " | $-C_2H_5$ | " | " |
| 135 | " | " | H | H | 2 | 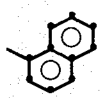 | " | " | " |
| 136 | " | " | H | H | 2 | " | " | $-C_2H_5$ | " |
| 137 | " | " | H | H | 2 | 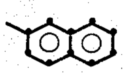 | " | " | " |
| 138 | $-C_2H_5$ | $-C_2H_5$ | H | H | 2 | " | " | " | " |
| 139 | $-C_2H_4CONH_2$ | " | H | H | 2 | " | " | " | " |
| 140 | $-C_2H_5$ | " | H | H | 1 | " | " | " | " |

Table IV-continued

| Ex. | $R_1$ | $R_5$ | $R_3$ | $R_6$ | X | Z' | $R_7$ | $R_{10}$ | I |
|---|---|---|---|---|---|---|---|---|---|
| 141 | " | " | H | H | 1 | 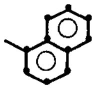 | " | " | " |
| 142 | " | " | $-CH_3$ | H | 1 | " | " | " | " |
| 143 | " | " | " | H | 1 | 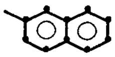 | " | " | " |
| 144 | $-C_2H_4CONH_2$ | " | " | H | 1 | " | " | " | " |
| 145 | " | " | H | H | 1 | " | " | " | " |
| 146 | $-CH_2-\underset{OH}{CH_2}$- | " | H | H | 1 | " | " | " | " |
| 147 | $-CH_2\underset{CH_3}{\underset{\mid}{C}}H-OH$ | " | H | H | 1 | " | " | " | " |

The structural composition of further dyes is shown in the following Table V; the dyes can be obtained in accordance with the procedure of Examples 1 and 2 and agree with the formula

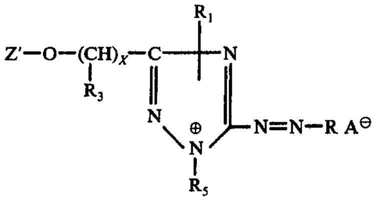

(e), in which Z', R, $R_1$, $R_3$, $R_5$ and X have the significances as given in the columns of the Table. A further column I indicates the dye shade on polyacrylonitrile, acid modified synthetic polyester and polyamide fibres. The anion $A^\ominus$ may be any one of those named in the foregoing description.

Table V

| Ex. | $R_1$ | $R_5$ | $R_3$ | X | Z' | R | I |
|---|---|---|---|---|---|---|---|
| 148 | $-CH_3$ | $-CH_3$ | H | 1 | 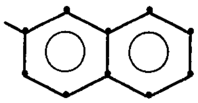 | 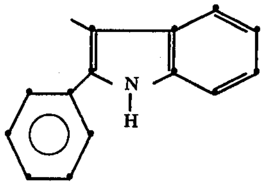 | reddish-yellow |
| 149 | " | " | H | 2 | " | " | " |
| 150 | " | " | H | 1 | " | 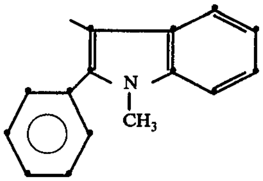 | " |
| 151 | " | " | $-CH_3$ | 1 | " | " | " |
| 152 | " | " | H | 2 | " | " | " |
| 153 | " | " | H | 1 | 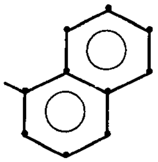 | " | " |
| 154 | " | " | $-CH_3$ | " | " | " | " |
| 155 | " | " | H | 2 | " | " | " |

Table V-continued

| Ex. | $R_1$ | $R_5$ | $R_3$ | X | Z' | R | I |
|---|---|---|---|---|---|---|---|
| 156 | " | " | H | 1 | " | 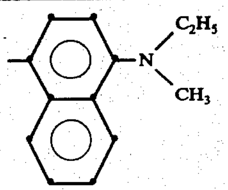 | bluish-violet |
| 157 | " | " | " | " | 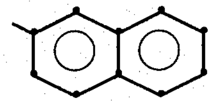 | " | " |
| 158 | " | " | " | " | " | 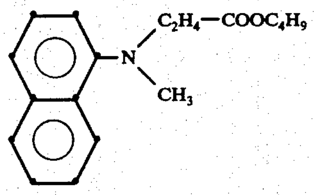 | " |
| 159 | " | " | $-CH_3$ | " | " | " | " |
| 160 | " | " | H | 2 | " | " | " |

EXAMPLE 161

27 Parts of 2-amino-5-phenoxymethyl-6-methoxybenzothiazole are dissolved in 100 parts of glacial acetic acid and mixed with 90 parts sulphuric acid with ice cooling so that the temperature does not rise above 35° to 40°. 100 Parts of ice are added and at −5° to 0° a mixture consisting of 7.3 parts of sodium nitrite and 25 parts of water are added dropwise. The mixture is stirred, with cooling for one hour and thereafter is mixed with a solution consisting of 14.9 parts of diethylaniline and 25 parts of glacial acetic acid. The reaction mixture is stirred at room temperature for 3 hours and then the pH is adjusted with 170 parts of a 30% aqueous sodium hydroxide solution, the temperature being kept under 35° with cooling. The resulting dye is filtered, washed thoroughly with water and dried at 50° under vacuum.

The above diazo component can, for example, be prepared from 3-phenoxymethyl-p-anisidine according to the Hugershoff'schen Benzothiazole-Synthesis. 21.5 Parts of the dried and pulverized dye are stirred into 200 parts of glacial acetic acid and mixed with 2.2 parts of magnesium oxide. The mixture is warmed to a temperature between 60° and 70°. Over a period of 15 minutes, 13.9 parts of dimethylsulphate are added dropwise and the mixture is stirred at 70° to 75° for 3 hours. The reaction mixture is diluted with 2000 parts of water and the dye is salted out by the addition of 14 parts of zinc chloride and 100 parts of sodium chloride. The dye is filtered, washed with 100 parts of a 5% aqueous sodium chloride solution and dried under vacuum at 50°. 25.6 Parts of the dye of the formula

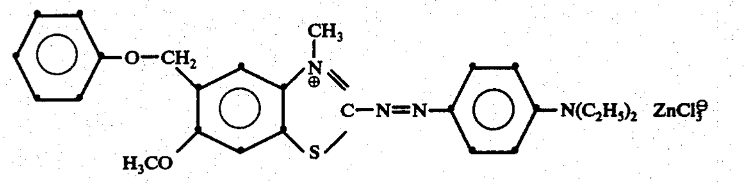

are obtained, which gives blue dyeings on polyacrylonitrile and acid modified polyester fibres.

| Ex. | | Dye-shade on polyacrylonitrile |
|---|---|---|
| 162 | 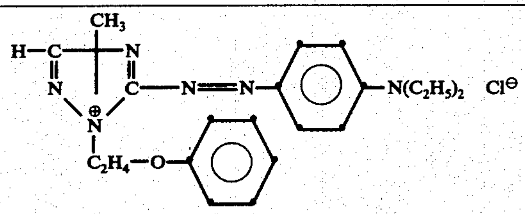 | bluish-red |

-continued

| Ex. | | Dye-shade on polyacrylonitrile |
|---|---|---|
| 163 | 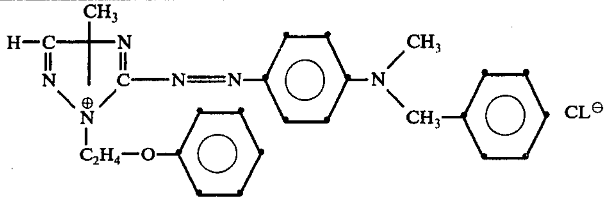 | " |
| 164 | 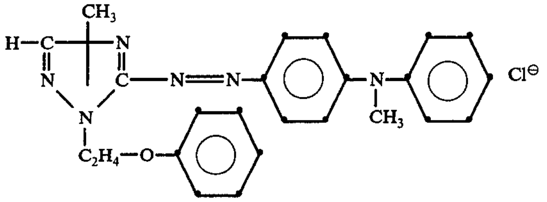 | rubine |
| 165 | 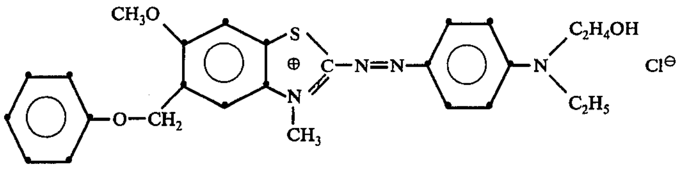 | greenish-blue |
| 166 | 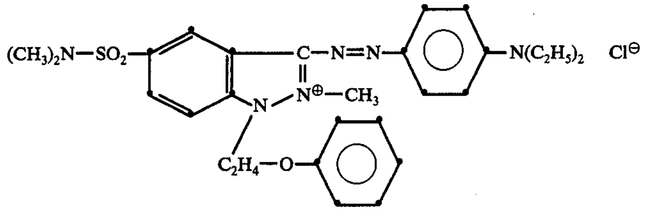 | violet |
| 167 | 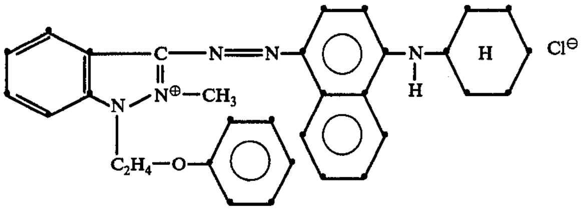 | blue |

APPLICATION EXAMPLE A

20 Parts of the salt of the dye described in Example 1 and 80 parts dextrin are ground for 4 hours in a powder mill. One part of the preparation so obtained is made into a paste with 1 part of 40% acetic acid. The same dyestuff mixture can also be formed into a paste with 100 parts of water and finally spray dried. 200 Parts of demineralized water are poured onto the paste and the mixture is boiled for a short time. It is then diluted with 7000 parts of demineralized water, mixed with 2 parts of glacial acetic acid and is put into a bath at 60° with 100 parts of polyacrylonitrile fabric. The fabric may be pretreated for 10–15 minutes at 60° in a bath consisting of 8000 parts of water and 2 parts of glacial acetic acid.

The dyebath is raised to 98°–100° over a period of 30 minutes, boiled for 1½ hours and the fabric rinsed. A bluish-red dyeing with good light fastness and wet fastness is obtained.

10 Parts of the dye mentioned in Example 1 are dissolved in 60 parts of glacial acetic acid and 30 parts of water. A stable concentrated solution, with about 10% dye content, is obtained, which solution can be used to dye polyacrylonitrile according to the above-mentioned process.

APPLICATION EXAMPLE B

20 Parts of the dye of Example 1 are mixed with 80 parts of dextrin in a ball-mill for 48 hours; 1 part of this product is made into a paste with 1 part of 40% acetic acid, 200 parts of demineralized water are poured onto the paste and the mixture is boiled for a short time. With this solution the following dyeings are obtained.

(a) The solution is diluted with 7000 parts of demineralized water and mixed with 21 parts of anhydrous sodium sulphate, 14 parts of ammonium sulphate, 14 parts of formic acid and 15 parts of a carrier based on the reaction product of ethylene oxide with dichlorophenolene are put into a bath at 60° with 100 parts of a polyester fabric, which fabric has been modified with acid groups. The fabric may be pretreated to 10 to 15 minutes at 60° in a bath consisting of 8000 parts of water and 2 parts of glacial acetic acid.

The dyebath is raised to 98°-100° over a period of 30 minutes, boiled for 1½ hours and the fabric rinsed. A similar bluish-red dyeing with good wet fastness is obtained.

(b) The solution is diluted with 3000 parts of demineralized water and mixed with 18 parts of anhydrous sodium sulphate, together with 6 parts of ammonium sulphate and formic acid and put into the bath at 60° with 100 parts of a polyester fabric, which fabric has been modified with acid groups. The closed vessel is heated to 110° over a period of 45 minutes, kept at this temperature for 1 hour with shaking, cooled at 60° within 25 minutes and the dyed fabric rinsed. A similar bluish-red dyeing with good wet fastness is obtained.

(c) The same procedure as described in paragraph (b) above is carried out except that the closed vessel is heated for 1 hour at 120°.

Formulae of representative dyes of the foregoing examples are as follows:

Example 1

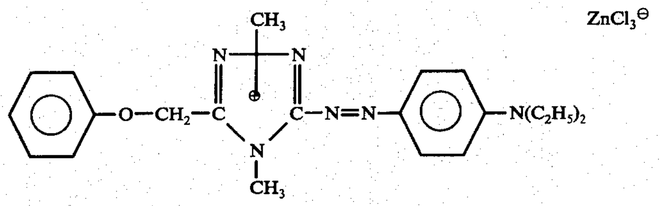

Example 32

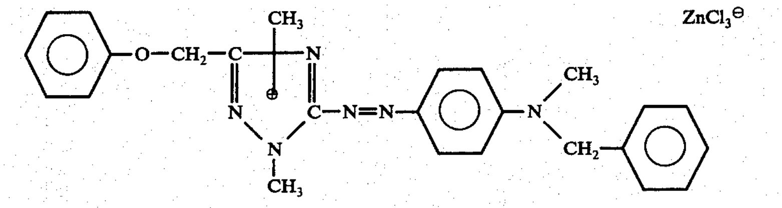

Example 50

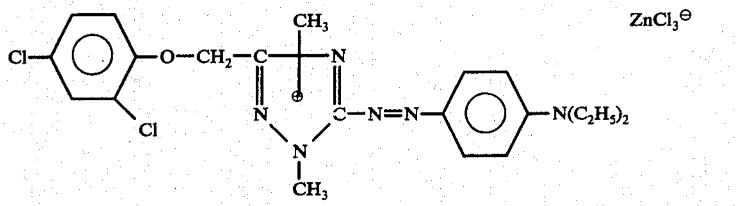

Example 60

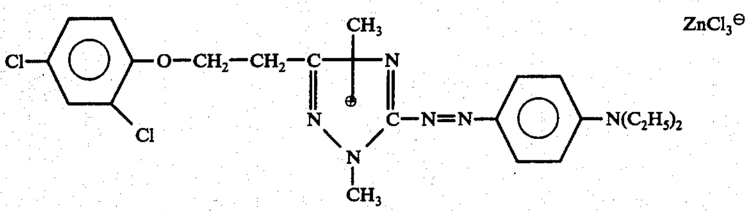

Example 78

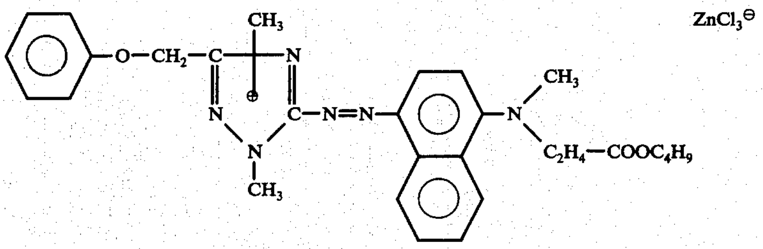

-continued
Example 89
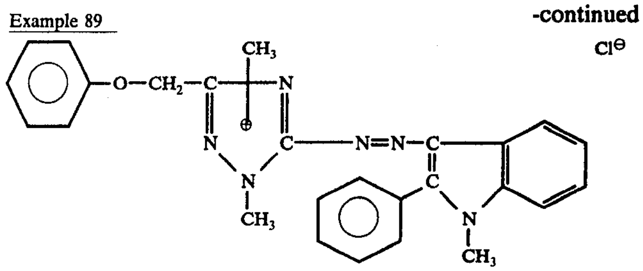
Example 124
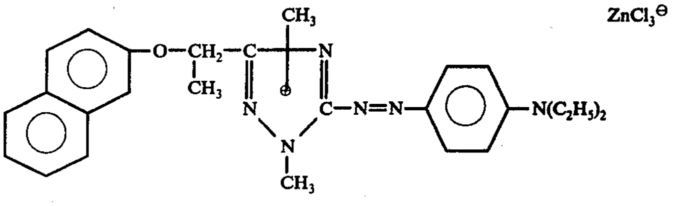
Example 137
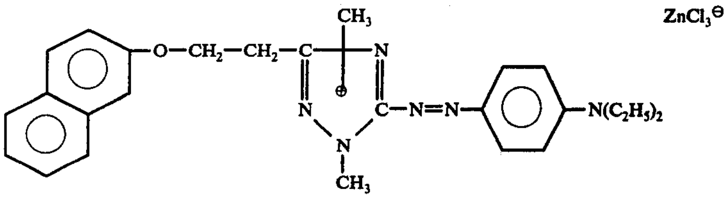
Example 162
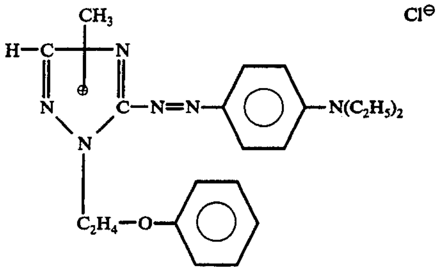
Example 163
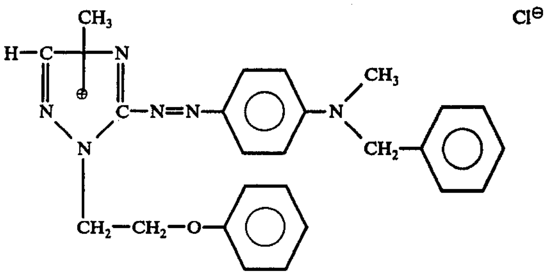
Example 165
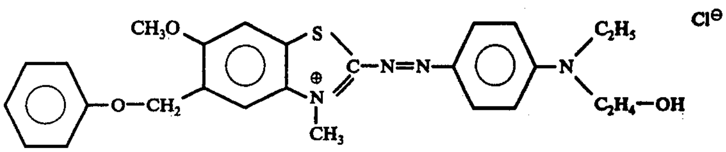
What is claimed is:
1. A compound of the formula

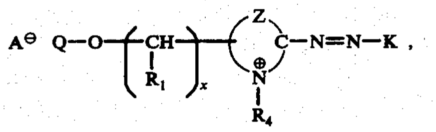

or a mixture thereof, wherein

Q is

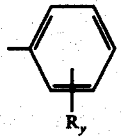 or 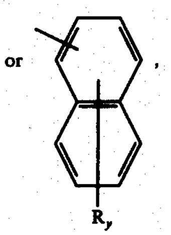 , wherein each R is independently hydroxy; halo; alkyl; alkyl substituted by halo, hydroxy, cyano, phenyl or phenoxy; alkoxy; alkoxy substituted by halo, hydroxy, cyano, phenyl or phenoxy; trifluoromethyl; cycloalkyl of 5 or 6 carbon atoms; substituted cycloalkyl of 5 or 6 carbon atoms each substituent of which is independently alkyl; cyano; nitro; phenoxy; naphthyloxy; phenylazo; —CORo; —CO—ORo; —CO—NH—Ro; —NH—CO—Ro; —CO—N(Ro)$_2$; —O—CO—Ro; —O—CO—NH—Ro; —O—CO—N(Ro)$_2$; —SO$_2$—Ro; —SO$_2$—NH—Ro; —SO$_2$—N(Ro)$_2$; —O—SO$_2$—NH—Ro; —O—SO$_2$—N(Ro)$_2$;

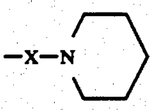 ; 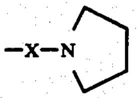 ;

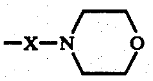 or 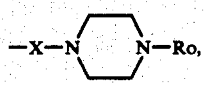 , wherein each Ro is independently alkyl or phenyl, and each X is independently —CO— or —SO$_2$—, and y is 0, 1, 2, 3, 4 or 5, each $R_1$ is independently hydrogen; alkyl; alkyl substituted by halo, alkoxy or phenoxy; phenyl or cycloalkyl of 5 or 6 carbon atoms,

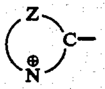

is thiazolium, isothiazolium, thiadiazolium, triazolium, imidazolium, indazolium, oxazolium, pyridinium, pyrimidinium, pyridazinium, pyrazinium, benzothiazolium, oxadiazolium, quinoxalinium, cinnolinium, quinolinium, phthalazinium, pyrazolium, benzoxazolium or benzimidazolium, or a substituted derivative thereof, wherein each substituent is independently alkyl; alkyl substituted by phenyl, phenoxy, hydroxy, carbamoyl, cycloalkyl of 5 or 6 carbon atoms, cyano or halo; alkoxy; alkoxy substituted by phenyl, phenoxy, hydroxy, carbamoyl, cycloalkyl of 5 or 6 carbon atoms, cyano or halo; alkenyl of 2 to 4 carbon atoms; alkenyl of 2 to 4 carbon atoms substituted by hydroxy, halo, cyano, phenyl or carbamoyl; cycloalkyl of 5 to 7 carbon atoms; substituted cycloalkyl of 5 to 7 carbon atoms each substituent of which is independently alkyl, alkoxy or halo; phenyl; substituted phenyl each substituent of which is independently cyano, nitro, alkyl, alkoxy or halo; phenoxy; substituted phenoxy each substituent of which is independently cyano, nitro, alkyl, alkoxy or halo; —CO—Ro; —CO—ORo; —CO—NH—Ro; —CO—N(Ro)$_2$; —NH—CO—Ro; —SO$_2$Ro; —SO$_2$—NH—Ro; —SO$_2$—N(Ro)$_2$; —NH—SO$_2$—Ro or phenylazo, wherein each Ro is independently alkyl or phenyl, $R_4$ is alkyl of 1 to 8 carbon atoms; alkyl of 1 to 8 carbon atoms substituted by halo, hydroxy, phenyl, cycloalkyl of 5 or 6 carbon atoms, alkoxy or carbamoyl; alkenyl of 2 to 8 carbon atoms; alkenyl of 2 to 8 carbon atoms substituted by halo, hydroxy, phenyl, cycloalkyl of 5 or 6 carbon atoms, alkoxy or carbamoyl; alkoxy; alkoxy substituted by halo, hydroxy, phenyl, cycloalkyl of 5 or 6 carbon atoms, alkoxy or carbomoyl; cycloalkyl of 5 or 6 carbon atoms or substituted cycloalkyl of 5 or 6 carbon atoms each substituent of which is independently alkyl, alkoxy, halo or hydroxy, K is a coupling component radical free of water-solubilizing groups, $x$ is 1, 2 or 3, and A⊖ is an anion, wherein each alkyl, alkoxy, alkyl moiety of each group and alkoxy moiety of each group independently has 1 to 4 carbon atoms unless otherwise indicated, and each halo is independently chloro, bromo or iodo.

2. A compound according to claim 1, or a mixture thereof, wherein

K is

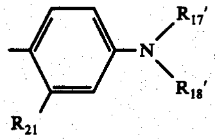 , 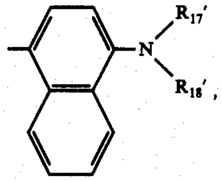 ,

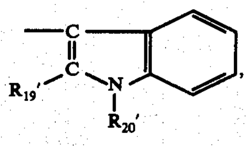 , 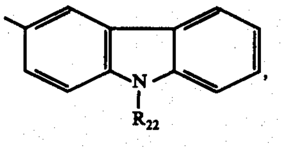 ,

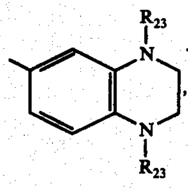 , 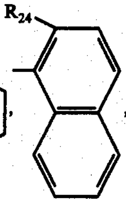 , 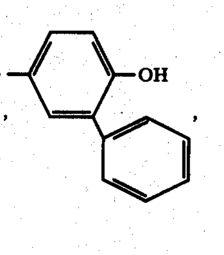 ,

-continued

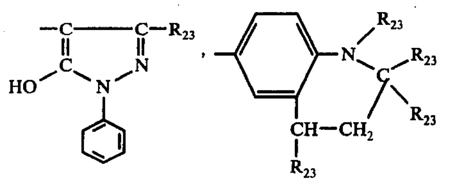

OR

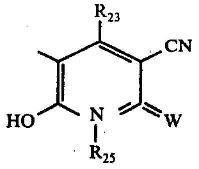

wherein each of $R_{17}'$ and $R_{18}'$ is independently hydrogen, cyclohexyl, phenyl, alkyl or alkyl substituted by alkoxycarbonyl, benzoyloxy, phenoxy, halo, hydroxy, phenyl, cyano, alkoxy, alkylcarbonyloxy or N,N-dialkylcarbamoyloxy, or $R_{17}'$ and $R_{18}'$ taken together and with the nitrogen atom to which they are joined are

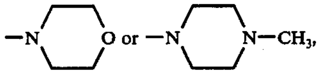

$R_{19}'$ is phenyl, alkyl or phenylalkyl, $R_{20}'$ is hydrogen, alkyl or phenyl, $R_{21}$ is hydrogen, alkyl, alkoxy or halo, $R_{22}$ is alkyl, each $R_{23}$ is independently alkyl, $R_{24}$ is amino, hydroxy or —NH—$R_{26}$, wherein $R_{26}$ is phenyl or phenyl substituted by one or two methyl groups, $R_{25}$ is hydrogen, alkyl or alkoxyalkyl, and W is =O or =NH.

3. A compound of the formula

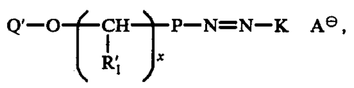

or a mixture thereof, wherein

Q' is

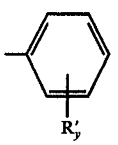

or

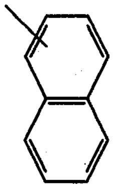

, wherein each R' is independently nitro; halo; hydroxy; cyano; trifluoromethyl; alkyl; alkyl substituted by phenyl or phenoxy; alkoxy; alkoxy substituted by phenyl or phenoxy; cyclohexyl; phenoxy; benzoyloxy; phenylazo; dialkylsulfamoyloxy; —CO—Ro; —CO—Oro; —CO—NH—Ro; —CO—N(Ro)$_2$; —O—CO—NH—Ro; —O—CO—N(Ro)$_2$; —NH—CO—Ro; —SO$_2$—Ro; —SO$_2$—NH—Ro; —SO$_2$—N(Ro)$_2$;

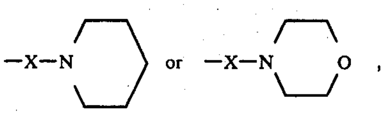

wherein each Ro is independently alkyl or phenyl, and each X is —CO— or —SO$_2$—, and Y is 0, 1, 2, 3, 4 or 5, with the proviso that each R' is halo when *y* is 3, 4 or 5, $R_1'$ is hydrogen, alkyl or phenyl, P is

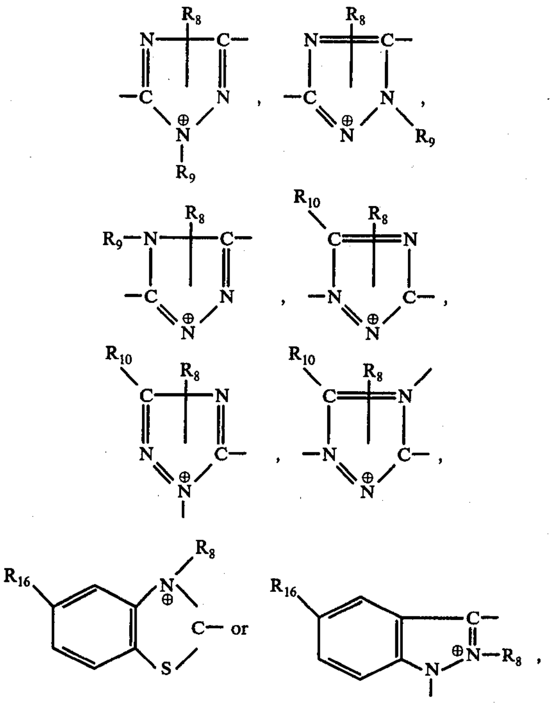

wherein $R_8$ is alkyl; alkyl substituted by hydroxy, halo, cyano, phenyl or carbamoyl; alkenyl of 2 to 4 carbon atoms; alkenyl of 2 to 4 carbon atoms substituted by hydroxy, halo, cyano, phenyl or carbamoyl; cyclohexyl or substituted cyclohexyl each substituent of which is independently alkyl, $R_9$ is alkyl; alkyl substituted by hydroxy, halo, cyano, phenyl or carbamoyl; alkenyl of 2 to 4 carbon atoms; alkenyl of 2 to 4 carbon atoms substituted by hydroxy, halo, cyano, phenyl or carbamoyl; cyclohexyl; substituted cyclohexyl each substituent of which is independently alkyl; phenyl or substituted phenyl each substituent of which is independently halo, alkyl or alkoxy, $R_{10}$ is hydrogen; alkyl; alkyl substituted by hydroxy, halo, cyano, phenyl or carbamoyl; alkenyl of 2 to 4 carbon atoms; alkenyl of 2 to 4 carbon atoms substituted by hydroxy, halo, cyano, phenyl or carbamoyl; cyclohexyl; substituted cyclohexyl each substituent of which is independently alkyl; phenyl or substituted phenyl each substituent of which is independently halo, alkyl or alkoxy, and $R_{16}$ is hyrdogen; halo; alkyl; alkyl substituted by phenyl, phenoxy, hydroxy, carbamoyl, cycloalkyl of 5 or 6 carbon atoms, cyano or halo; alkoxy; alkoxy substituted by phenyl, phenoxy, hydroxy, carbamoyl, cycloalkyl of 5 or 6 carbon atoms, cyano or halo; phenoxy; —CO—Ro; —CO—ORO; —CO—NH—Ro; —CO—N(Ro)$_2$; —NH—CO—Ro; —SO$_2$—Ro; —SO$_2$—NHRo; —SO$_2$—N(Ro)$_2$ or —NH—SO$_2$—Ro, wherein each Ro is independently alkyl or phenyl, K is a coupling component radical free of water-solubilizing groups, $x$ is 1, 2 or 3, and A⊖ is an anion, wherein each alkyl, alkoxy, alkyl moiety of each group and alkoxy moiety of each group independently has 1 to 4 carbon atoms unless otherwise indicated, and each halo is independently chloro, bromo or iodo.

4. A compound according to claim 3, or a mixture thereof, wherein

K is

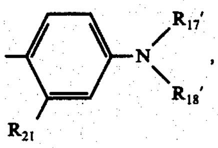
,
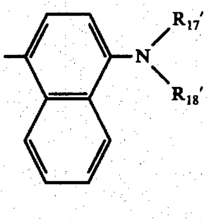
,

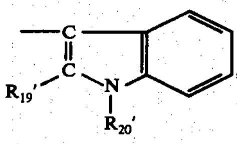
,
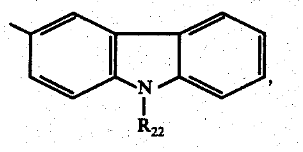
,

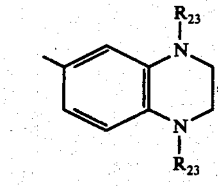
,
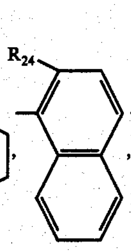
,
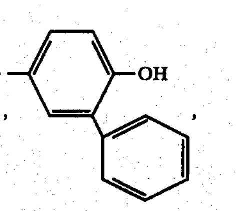
,

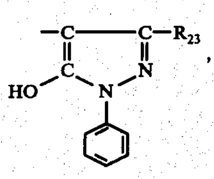
,
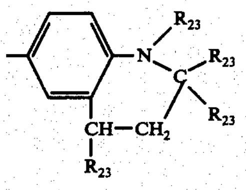

OR
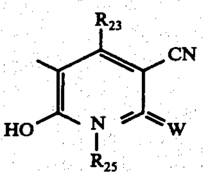
, wherein each of $R_{17}'$ and $R_{18}'$ is independently hydrogen, cyclohexyl, phenyl, alkyl or alkyl substituted by alkoxycarbonyl, benzoyloxy, phenoxy, halo, hydroxy, phenyl, cyano, alkoxy, alkylcarbonyloxy or N,N-dialkylcarbamoyloxy, or $R_{17}'$ and $R_{18}'$ taken together and with the nitrogen atom to which they are joined are

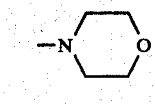
or
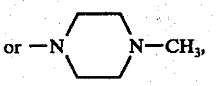
, $R_{19}'$ is phenyl, alkyl or phenylalkyl, $R_{20}'$ is hydrogen, alkyl or phenyl, $R_{21}$ is hydrogen, alkyl, alkoxy or halo, $R_{22}$ is alkyl, each $R_{23}$ is independently alkyl, $R_{24}$ is amino, hydroxy or —NH—$R_{26}$, wherein $R_{26}$ is phenyl or phenyl substituted by one or two methyl groups, $R_{25}$ is hydrogen, alkyl or alkoxyalkyl, and W is =O or =NH.

5. A compound according to claim 4 having the formula

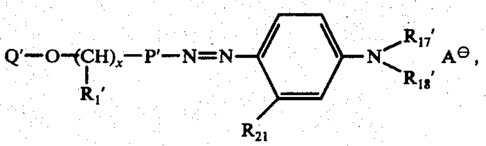

or a mixture thereof, wherein

P' is

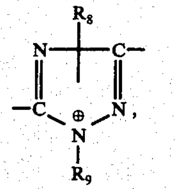
,

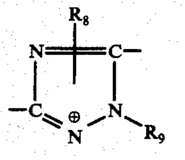

or

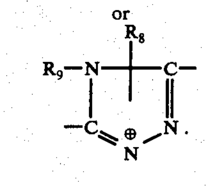
.

6. A compound according to claim 4, or a mixture thereof, wherein each R' is independently nitro; halo; hydroxy; cyano; trifluoromethyl; alkyl; alkyl substituted by phenyl or phenoxy; alkoxy; alkoxy substituted by phenyl or phenoxy; —CO—Ro; —CO—ORo; —CO—NH—Ro; —CO—N(Ro)$_2$; —NH—CO—Ro; —SO$_2$—Ro; —SO$_2$NH—Ro; —SO$_2$—N(Ro)$_2$;

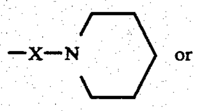
or
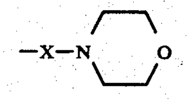
, wherein each Ro is independently alkyl or phenyl, and each X is —CO— or —$SO_2$—, $R_8$ is alkyl; alkyl substituted by hydroxy, halo, cyano, phenyl or carbamoyl; alkenyl of 2 to 4 carbon atoms; alkenyl of 2 to 4 carbon atoms substituted by hydroxy, halo, cyano, phenyl, or carbamoyl; cyclohexyl or cyclohexyl substituted by alkyl, $R_9$ is alkyl; alkyl substituted by hydroxy, halo, cyano, phenyl or carbamoyl; alkenyl of 2 to 4 carbon atoms; alkenyl of 2 to 4 carbon atoms substituted by hydroxy, halo, cyano, phenyl or carbamoyl; cyclohexyl; cyclohexyl substituted by alkyl; phenyl or phenyl substituted by halo, alkyl or alkoxy, and $R_{10}$ is hydrogen; alkyl; alkyl substituted by hydroxy, halo, cyano, phenyl or carbamoyl; alkenyl of 2 to 4 carbon atoms; alkenyl of 2 to 4 carbon atoms substituted by hydroxy, halo, cyano, phenyl or carbamoyl; cyclohexyl; cyclohexyl substituted by alkyl; phenyl or phenyl substituted by halo, alkyl or alkoxy.

7. A compound according to claim 3 having the formula

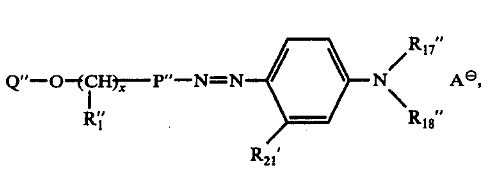

or a mixture thereof, wherein

P'' is

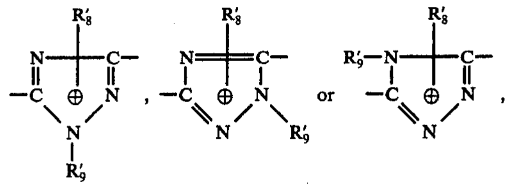

Q'' is

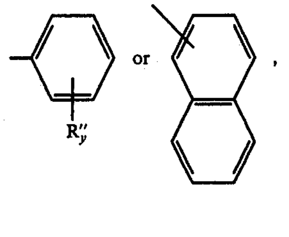

wherein each R'' is independently hydroxy, benzoyl, halo, alkyl, alkoxy, nitro, trifluoromethyl, alkylcarbonyl, cyano, alkoxycarbonyl, benzoyloxy, alkylsulfonyl, dialkylsulfamoyl, dialkylsulfamoyloxy, benzamido, phenylsulfonyl, benzyl, cyclohexyl, phenoxy, phenylcarbamoyloxy, alkylcarbamoyloxy, N-phenyl-N-alkylcarbamoyloxy, phenoxymethyl or phenylazo, and $y$ is 0, 1, 2, 3, 4 or 5, with the proviso that each R'' is halo when $y$ is 3, 4 or 5, $R_1''$ is hydrogen or methyl, $R_8'$ is alkyl or alkyl substituted by hydroxy or carbamoyl, $R_9'$ is alkyl, alkyl substituted by hydroxy or carbamoyl or cyclohexyl, each of $R_{17}''$ and $R_{18}''$ is independently phenyl, alkyl or alkyl substituted by alkoxycarbonyl, benzoyloxy, phenoxy, halo, hydroxy, phenyl, cyano, alkoxy or alkylcarbonyloxy, or $R_{17}''$ and $R_{18}''$ taken together and with the nitrogen atom to which they are joined are morpholino or N'-methylpiperazino, $R_{21}'$ is hydrogen, alkyl, alkoxy or halo, and $x'$ is 1, 2 or 3.

8. A compound according to claim 4 having the formula

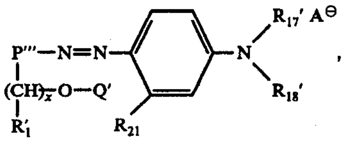

or a mixture thereof, wherein

P''' is

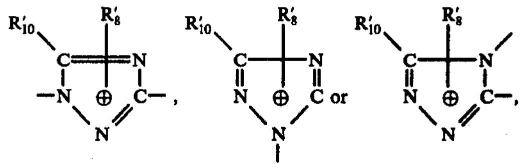

$R_8'$ is alkyl or alkyl substituted by hydroxy or carbamoyl, and $R_{10}'$ is hydrogen, alkyl, alkyl substituted by hydroxy or carbamoyl or cyclohexyl.

9. A compound according to claim 8 having the formula

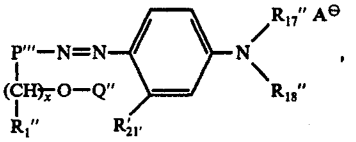

or a mixture thereof, wherein

P''' is

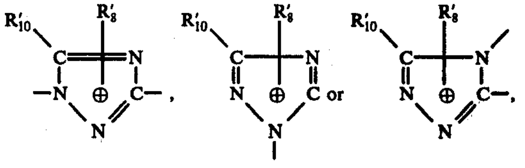

Q'' is

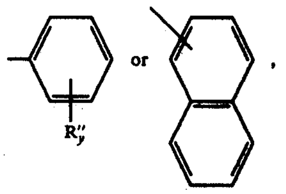

wherein each $R''$ is independently hydroxy, benzoyl, halo, alkyl, alkoxy, nitro, trifluoromethyl, alkylcarbonyl, cyano, alkoxycarbonyl, benzoyloxy, alkylsulfonyl, dialkylsulfamoyl, dialkylsulfamoyloxy, benzamido, phenylsulfonyl, benzyl, cyclohexyl, phenoxy, phenylcarbamoyloxy, alkylcarbamoyloxy, N-phenyl-N-alkylcarbamoyloxy, phenoxymethyl or phenylazo, and $y$ is 0, 1, 2, 3, 4 or 5, with the proviso that each $R''$ is halo when $y$ is 3, 4 or 5, $R_1''$ is hydrogen or methyl, $R_8'$ is alkyl or alkyl substituted by hydroxy or carbamoyl, $R_{10}'$ is hydrogen, alkyl, alkyl substituted by hydroxy or carbamoyl or cyclohexyl, each of $R_{17}''$ and $R_{18}''$ is independently phenyl, alkyl or alkyl substituted by alkoxycarbonyl, benzoyloxy, phenoxy, halo, hydroxy, phenyl, cyano, alkoxy or alkylcarbonyloxy, or $R_{17}''$ and $R_{18}''$ taken together and with the nitrogen atom to which they are joined are morpholino or N′-methylpiperazino, $R_{21}'$ is hydrogen, alkyl, alkoxy or halo, and $x'$ is 1, 2 or 3.

10. A compound according to claim 7 having the formula

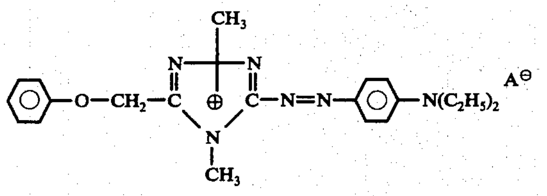

11. A compound according to claim 7 having the formula

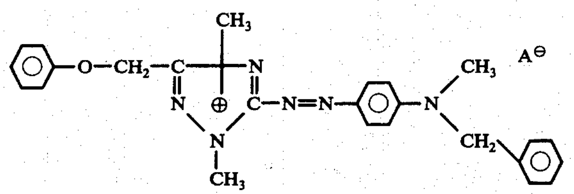

12. A compound according to claim 7 having the formula

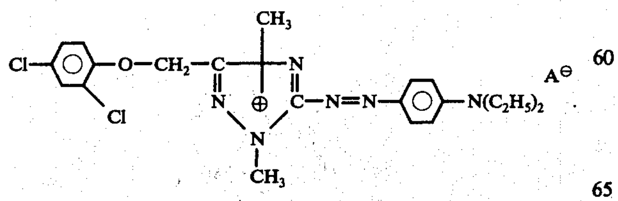

13. A compound according to claim 7 having the formula

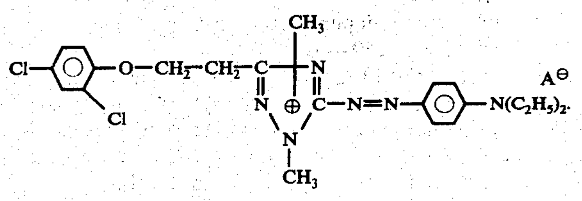

14. A compound according to claim 4 having the formula

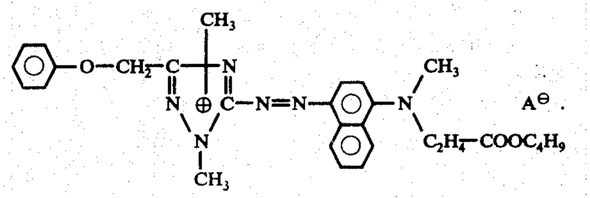

15. A compound according to claim 4 having the formula

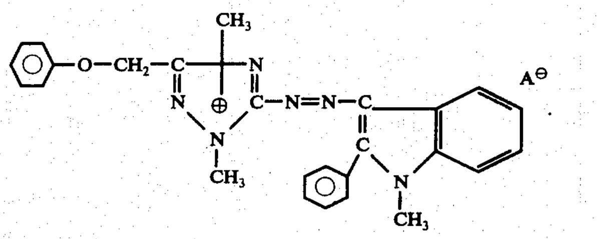

16. A compound according to claim 7 having the formula

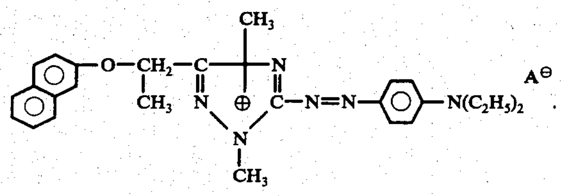

17. A compound according to claim 7 having the formula

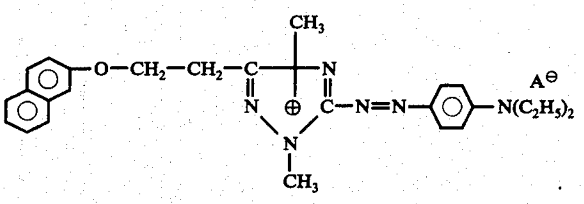

18. A compound according to claim 9 having the formula

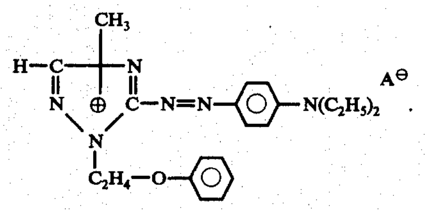

19. A compound according to claim 9 having the formula
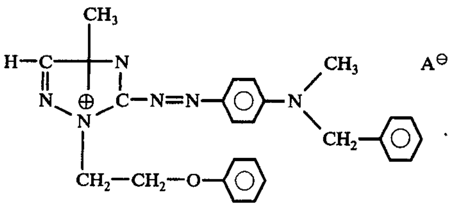
20. A compound according to claim 4 having the formula
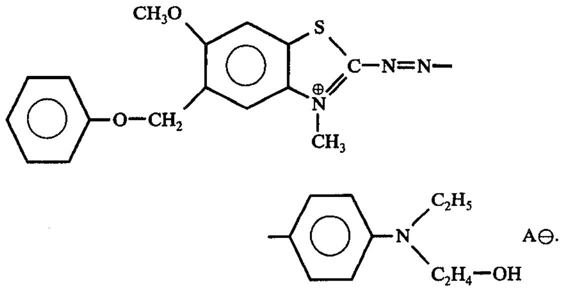
* * * * *